(12) United States Patent
Cecchetto et al.

(10) Patent No.: US 12,102,515 B2
(45) Date of Patent: Oct. 1, 2024

(54) LAMINATE WEBS AND ABSORBENT ARTICLES HAVING THE SAME

(71) Applicant: The Procter & Gamble Company, Cincinnati, OH (US)

(72) Inventors: Pietro Cecchetto, Fairfield, OH (US); Linda Ann Sauer, Cincinnati, OH (US); Shihuang Li, Xiamen (CN)

(73) Assignee: The Procter & Gamble Company, Cincinnati, OH (US)

( * ) Notice: Subject to any disclaimer, the term of this patent is extended or adjusted under 35 U.S.C. 154(b) by 72 days.

(21) Appl. No.: 17/030,587

(22) Filed: Sep. 24, 2020

(65) Prior Publication Data
US 2021/0007907 A1 Jan. 14, 2021

Related U.S. Application Data

(63) Continuation of application No. 16/015,234, filed on Jun. 22, 2018, now Pat. No. 10,813,797.

(30) Foreign Application Priority Data

Jun. 22, 2017 (WO) ............... PCT/CN2017/089550
Jun. 22, 2017 (WO) ............... PCT/CN2017/089553
(Continued)

(51) Int. Cl.
*A61F 13/511* (2006.01)
*A61F 13/512* (2006.01)
(Continued)

(52) U.S. Cl.
CPC .. *A61F 13/51104* (2013.01); *A61F 13/51108* (2013.01); *A61F 13/5116* (2013.01);
(Continued)

(58) Field of Classification Search
None
See application file for complete search history.

(56) References Cited

U.S. PATENT DOCUMENTS 3,929,135 A * 12/1975 Thompson ............... B32B 3/28
604/374
3,967,623 A 7/1976 Butterworth
(Continued)

FOREIGN PATENT DOCUMENTS

CN 1875899 A 12/2006
CN 1942520 A 4/2007
(Continued)

OTHER PUBLICATIONS

Machine Translation of JP-04024263-A, Jan. 1992 (Year: 1992).*
(Continued)

*Primary Examiner* — Jeffrey A Vonch
(74) *Attorney, Agent, or Firm* — Sarah M. DeCristofaro; George Leal; William E. Gallagher

(57) ABSTRACT

A laminate web having a polymer film layer and a nonwoven layer is disclosed. The polymer film layer makes up a first side of the laminate web and the nonwoven layer makes up a second side of the laminate web. The laminate web has a plurality of first elements extending from the polymer film. The web also has a plurality of second elements formed outwardly from the first side of the laminate web.

8 Claims, 23 Drawing Sheets

(30) Foreign Application Priority Data

Jun. 22, 2017 (WO) ................ PCT/CN2017/089554
Dec. 20, 2017 (WO) ................ PCT/CN2017/117407

(51) Int. Cl.
| | |
|---|---|
| *B32B 3/24* | (2006.01) |
| *B32B 3/26* | (2006.01) |
| *B32B 3/28* | (2006.01) |
| *B32B 3/30* | (2006.01) |
| *B32B 5/02* | (2006.01) |
| *B32B 27/02* | (2006.01) |
| *B32B 27/12* | (2006.01) |
| *B32B 37/15* | (2006.01) |
| *A61F 13/15* | (2006.01) |
| *A61F 13/51* | (2006.01) |
| *B32B 27/32* | (2006.01) |
| *B32B 37/00* | (2006.01) |
| *B32B 38/04* | (2006.01) |
| *B32B 38/06* | (2006.01) |

(52) U.S. Cl.
CPC ........ *A61F 13/512* (2013.01); *A61F 13/5123* (2013.01); *B32B 3/266* (2013.01); *B32B 3/28* (2013.01); *B32B 3/30* (2013.01); *B32B 5/022* (2013.01); *B32B 27/02* (2013.01); *B32B 27/12* (2013.01); *B32B 37/153* (2013.01); *A61F 2013/15715* (2013.01); *A61F 13/15731* (2013.01); *A61F 2013/51078* (2013.01); *A61F 2013/51165* (2013.01); *A61F 13/5121* (2013.01); *A61F 13/5125* (2013.01); *A61F 2013/5127* (2013.01); *B32B 27/32* (2013.01); *B32B 2037/0092* (2013.01); *B32B 2038/047* (2013.01); *B32B 38/06* (2013.01); *B32B 2262/0253* (2013.01); *B32B 2307/726* (2013.01); *B32B 2555/02* (2013.01); *Y10T 428/24281* (2015.01); *Y10T 428/24289* (2015.01); *Y10T 428/24322* (2015.01); *Y10T 428/24331* (2015.01); *Y10T 428/24612* (2015.01); *Y10T 428/24628* (2015.01); *Y10T 442/674* (2015.04)

(56) References Cited

U.S. PATENT DOCUMENTS

| | | | |
|---|---|---|---|
| 4,041,951 A | 8/1977 | Sanford | |
| 4,324,247 A | 4/1982 | Aziz | |
| 4,342,314 A * | 8/1982 | Radel | A61F 13/51121 428/116 |
| 4,609,518 A * | 9/1986 | Curro | B29C 51/225 425/290 |
| 4,614,679 A | 9/1986 | Farrington, Jr. | |
| 4,626,254 A | 12/1986 | Widlund | |
| 4,629,457 A * | 12/1986 | Ness | A61F 13/15699 604/382 |
| 4,629,643 A | 12/1986 | Curro | |
| 4,798,604 A * | 1/1989 | Carter | C08J 5/18 604/383 |
| 5,023,124 A * | 6/1991 | Kobayashi | A61F 13/51305 428/913 |
| 5,078,710 A | 1/1992 | Suda | |
| 5,368,909 A | 11/1994 | Langdon | |
| 5,368,910 A | 11/1994 | Langdon | |
| H1670 H * | 7/1997 | Aziz | A61F 13/51121 604/367 |
| 5,674,211 A | 10/1997 | Ekdahl | |
| 5,693,037 A * | 12/1997 | Lee | A61F 13/5123 604/382 |
| 5,919,177 A * | 7/1999 | Georger | B32B 27/32 428/152 |
| 5,935,682 A | 8/1999 | Wallstroem | |
| 6,096,016 A | 8/2000 | Tsuji | |
| 6,114,595 A | 9/2000 | Moore et al. | |
| 6,115,695 A | 9/2000 | Kern | |
| 6,168,849 B1 * | 1/2001 | Braverman | B32B 5/26 428/218 |
| 6,228,462 B1 * | 5/2001 | Lee | A61F 13/512 428/137 |
| 6,417,426 B1 | 7/2002 | Takai | |
| 6,503,598 B1 | 1/2003 | Goda | |
| 7,102,054 B1 | 9/2006 | Cree | |
| 9,803,301 B1 * | 10/2017 | Maschino | A61F 13/15699 |
| 10,258,517 B1 * | 4/2019 | Maschino | B32B 3/30 |
| 10,813,797 B2 | 10/2020 | Cecchetto et al. | |
| 2001/0014796 A1 | 8/2001 | Mizutani | |
| 2002/0026169 A1 | 2/2002 | Takai | |
| 2002/0052582 A1 * | 5/2002 | Takai | A61F 13/512 604/358 |
| 2003/0003269 A1 * | 1/2003 | Lee | B29C 48/0022 264/156 |
| 2004/0122396 A1 * | 6/2004 | Maldonado | B32B 3/28 604/383 |
| 2004/0161586 A1 * | 8/2004 | Cree | A61F 13/51104 428/137 |
| 2004/0247833 A1 * | 12/2004 | Copat | B26F 1/26 428/156 |
| 2005/0209575 A1 | 9/2005 | Stone et al. | |
| 2005/0234417 A1 | 10/2005 | Yoshimasa | |
| 2007/0196601 A1 | 8/2007 | Ray | |
| 2007/0212545 A1 * | 9/2007 | Cree | B32B 3/266 156/60 |
| 2007/0255247 A1 | 11/2007 | Moberg-Alehammar | |
| 2008/0132136 A1 * | 6/2008 | Uematsu | D04H 1/54 264/109 |
| 2008/0221538 A1 | 9/2008 | Zhao et al. | |
| 2008/0221541 A1 | 9/2008 | Lavash | |
| 2008/0294135 A1 | 11/2008 | Hara | |
| 2009/0026651 A1 | 1/2009 | Lee | |
| 2009/0137976 A1 | 5/2009 | Suzuki | |
| 2009/0221979 A1 * | 9/2009 | Huang | A61F 13/5126 604/385.101 |
| 2009/0247977 A1 | 10/2009 | Takeuchi | |
| 2009/0302504 A1 * | 12/2009 | Di Berardino | B26D 7/1863 264/48 |
| 2010/0036339 A1 * | 2/2010 | Hammons | A61F 13/5121 604/378 |
| 2010/0036347 A1 | 2/2010 | Hammons | |
| 2010/0036349 A1 | 2/2010 | Hammons | |
| 2010/0069867 A1 | 3/2010 | Noda | |
| 2010/0247844 A1 | 9/2010 | Curro | |
| 2010/0249740 A1 * | 9/2010 | Miyamoto | D04H 1/76 428/166 |
| 2010/0255258 A1 * | 10/2010 | Curro | B32B 5/142 428/156 |
| 2010/0312209 A1 * | 12/2010 | Kashiwagi | A61F 13/15731 156/60 |
| 2011/0118691 A1 | 5/2011 | Nishitani | |
| 2011/0151185 A1 * | 6/2011 | Cree | B32B 27/08 428/137 |
| 2011/0183109 A1 * | 7/2011 | Seyler | A61F 13/53708 428/132 |
| 2011/0196330 A1 | 8/2011 | Hammons | |
| 2011/0221094 A1 * | 9/2011 | Gross | B26F 1/24 264/284 |
| 2011/0223388 A1 | 9/2011 | Stone et al. | |
| 2011/0223399 A1 | 9/2011 | Adachi | |
| 2012/0003423 A1 * | 1/2012 | Cree | A61F 13/512 428/137 |
| 2012/0064280 A1 * | 3/2012 | Hammons | B29C 66/83411 383/105 |
| 2012/0064298 A1 | 3/2012 | Orr | |
| 2012/0238984 A1 | 9/2012 | Paldey | |
| 2012/0273997 A1 * | 11/2012 | Stone | A61F 13/15731 264/280 |
| 2012/0277701 A1 | 11/2012 | Stone | |
| 2014/0120323 A1 | 5/2014 | Lake et al. | |
| 2014/0296815 A1 | 10/2014 | Takken | |

(56) References Cited

U.S. PATENT DOCUMENTS

| | | | |
|---|---|---|---|
| 2015/0038933 | A1 | 2/2015 | Day |
| 2015/0273793 | A1 | 10/2015 | Thomas |
| 2015/0297415 | A1 | 10/2015 | Huang |
| 2016/0038351 | A1 | 2/2016 | Cecchetto |
| 2016/0074259 | A1 | 3/2016 | Rosati et al. |
| 2016/0076181 | A1 | 3/2016 | Strube |
| 2016/0076184 | A1* | 3/2016 | Orr .................. A61F 13/53743 428/178 |
| 2016/0158071 | A1 | 6/2016 | Barda |
| 2016/0158074 | A1 | 6/2016 | Norimoto |
| 2016/0257091 | A1* | 9/2016 | Fornoni ................. B32B 3/30 |
| 2017/0258645 | A1 | 9/2017 | Orr |
| 2017/0297292 | A1* | 10/2017 | Maschino ................ B32B 3/04 |
| 2018/0177643 | A1 | 6/2018 | Hao |
| 2018/0256414 | A1* | 9/2018 | Maschino ............... B32B 27/08 |
| 2020/0060882 | A1* | 2/2020 | Cecchetto ........... A61F 13/5123 |
| 2020/0397628 | A1* | 12/2020 | Gwag .................... B32B 21/10 |
| 2023/0390125 | A1 | 12/2023 | Cecchetto |

FOREIGN PATENT DOCUMENTS

| | | | | |
|---|---|---|---|---|
| CN | 1943530 | A * | 4/2007 | |
| CN | 2905008 | Y * | 5/2007 | |
| CN | 2912578 | Y | 6/2007 | |
| CN | 101438987 | A | 5/2009 | |
| CN | 102140759 | A * | 8/2011 | |
| CN | 102555312 | A | 7/2012 | |
| CN | 105411749 | A * | 3/2016 | |
| CN | 105496658 | | 4/2016 | |
| CN | 105581870 | A * | 5/2016 | |
| CN | 106064490 | A * | 11/2016 | ............... B26F 1/24 |
| CN | 106313867 | A * | 1/2017 | |
| CN | 107718528 | A * | 2/2018 | ............... B26F 1/24 |
| DE | 3919166 | A1 * | 12/1990 | ....... A61F 13/00008 |
| DE | 4437165 | A1 * | 4/1996 | .......... A61F 13/512 |
| EP | 0165807 | A1 * | 12/1985 | |
| EP | 489205 | A1 * | 6/1992 | .......... A61F 13/512 |
| EP | 0738505 | A1 | 10/1996 | |
| EP | 749740 | A1 * | 12/1996 | .......... A61F 13/512 |
| EP | 1022007 | A2 * | 7/2000 | .......... A61F 13/5116 |
| JP | S6472745 | A | 3/1989 | |
| JP | 02102046 | A * | 4/1990 | |
| JP | 02193663 | A * | 7/1990 | |
| JP | 04024263 | A * | 1/1992 | |
| JP | 04052130 | A | 2/1992 | |
| JP | 05125647 | A * | 5/1993 | |
| JP | H05125647 | A | 5/1993 | |
| JP | 05228173 | A * | 9/1993 | |
| JP | 06330443 | A | 11/1994 | |
| JP | 2647858 | B2 * | 8/1997 | ........ A61F 13/51104 |
| JP | 2002173863 | A * | 6/2002 | |
| JP | 2003000639 | A | 1/2003 | |
| JP | 2003116909 | A * | 4/2003 | |
| JP | 2004275296 | A * | 10/2004 | |
| JP | 2006061174 | A * | 3/2006 | |
| JP | 04187146 | A | 7/2006 | |
| JP | 2010063649 | A * | 3/2010 | |
| JP | 2010094320 | A | 4/2010 | |
| JP | 2013078376 | A | 5/2013 | |
| JP | 5829349 | B1 | 10/2015 | |
| JP | 6206269 | B2 | 10/2017 | |
| KR | 20110133188 | A | 12/2011 | |
| KR | 2012018038 | A * | 2/2012 | |
| TW | 201225940 | A * | 7/2012 | |
| WO | WO-9110415 | A2 * | 7/1991 | |
| WO | WO-9311725 | A1 * | 6/1993 | ....... A61F 13/47218 |
| WO | 9700656 | A1 | 1/1997 | |
| WO | WO-9702133 | A2 * | 1/1997 | ....... A61F 13/15699 |
| WO | 1997011661 | A1 | 4/1997 | |
| WO | WO-0025714 | A1 * | 5/2000 | ....... A61F 13/51121 |
| WO | WO-0059438 | A1 * | 10/2000 | ........... A61F 13/512 |
| WO | WO-0117475 | A1 * | 3/2001 | ....... A61F 13/15203 |
| WO | 2005000177 | A1 | 1/2005 | |
| WO | 2008058450 | A1 | 5/2008 | |
| WO | 2010017353 | A1 | 2/2010 | |
| WO | 2010110875 | A1 | 9/2010 | |
| WO | 2011075669 | A2 | 6/2011 | |
| WO | WO-2011080643 | A2 * | 7/2011 | ....... A61F 13/15699 |
| WO | 201214957 | | 2/2012 | |
| WO | 2012024576 | A1 | 2/2012 | |
| WO | WO-2013047868 | A1 * | 4/2013 | ....... A61F 13/15723 |

OTHER PUBLICATIONS

Machine Translation of JP-05125647-A, May 1993 (Year: 1993).*
Machine Translation of JP-2647858-B2, Aug. 1997 (Year: 1997).*
Machine Translation of JP-2003116909-A, Apr. 2003 (Year: 2003).*
Machine Translation of CN-1943530-A, Apr. 2007 (Year: 2007).*
Machine Translation of CN-106064490-A, Nov. 2016 (Year: 2016).*
Supplementary International Search Report and Written Opinion; Application Ser. No. PCT/CN2017/117407; dated Oct. 22, 2019; 14 pages.
International Search Report for PCT/ZCN2017/117407 dated Dec. 20, 2017.
All Office Actions for U.S. Appl. No. 16/015,234, filed Jun. 22, 2018.
All Office Actions; U.S. Appl. No. 18/330,682, filed Jun. 7, 2023.

* cited by examiner

LAMINATE WEBS AND ABSORBENT ARTICLES HAVING THE SAME

FIELD OF THE INVENTION

The present invention is directed to laminate webs comprising a polymer film having microtextures and a nonwoven, and absorbent articles comprising the laminate web.

BACKGROUND OF THE INVENTION

Laminates of webs such as films and fibrous webs are known in the art. For example, nonwoven webs are often laminated with polymer films such that they are useful as materials in disposable products such as topsheets on disposable absorbent articles. The laminate can be structured such that a skin-facing side of the laminate, when used in absorbent articles, is the polymer film. The laminate also can be structured in absorbent articles such that the polymer film is oriented as a garment-facing side. Polymer film is desirable to have a microtextured, preferably apertured three-dimensional surface which can provide the surface of the laminate web with a desirable feel (e.g., soft, silky), visual impression, and/or audible impression, as well as one or more desirable properties such as improved fluid handling.

Webs exhibiting a desirable feel can be made by forming microtextures such as protrusions and recesses in the webs via technologies such as a vacuum forming process and embossing process.

Laminate webs having a microtextured film are utilized in a wide variety of industrial and consumer products. Such laminate webs are known for use in disposable absorbent articles such as disposable diapers and feminine hygiene articles such as sanitary napkins, and the like. Such articles typically have a fluid pervious topsheet, a fluid impervious breathable backsheet, and optionally an absorbent core disposed between the topsheet and the backsheet. Laminate webs having a microtextured film layer and a nonwoven layer can be made to form a fluid pervious topsheet that transports fluid from the body facing surface of the sanitary napkin more deeply into the sanitary napkin or diaper towards the absorbent core.

Laminate webs comprising a microtextured polymer film layer can be further deformed to have two-dimensional or three-dimensional macro structures improving fluid transport such as apertures for improving fluid drainage.

One approach as an effort to improve the ability of fluid drainage in a laminate having a film layer and nonwoven web is to expose fibers extended from the nonwoven web. U.S. Pat. No. 8,273,943 discloses an absorbent article provided with a composite sheet which comprises a film sheet having multiple pores formed therein a fiber mass laminated on one side of the film sheet, wherein the fiber mass has a projected section in which a part of the fiber mass projects through the multiple pores toward the other side of the film sheet. WO2010/117636 discloses a laminate web having a nonwoven web and a microtextured polymer film, wherein the laminate web has a first side comprising the polymer film having caps and tufts including fibers extending from the nonwoven web. Each of the caps is an integral extension of the polymer film and having at least one opening including a location of rupture in the polymer film above which the tuft extends. The exposed fibers extended from nonwoven web acquire and retain some fluid in small capillaries that might exist between the fibers which may be visually perceptible to the user of the product as an undesirable stain.

However, even with formation of macro apertures for improving fluid transport in a microtextured web, there still is a challenge in fluid drainage especially when the polymer film layer has microprotrusions, as fluid tends to be trapped in valleys between the microprotrusions. Especially when microtextures are in the form of discrete extended elements like protrusions, in case the microtextured web is used as a topsheet of absorbent articles, fluid tends to be trapped in valleys among the discrete extended elements. Trapped fluid may be visually perceptible to the user of the product and the user may misinterpret the staining as an indication that the utility of the product is exhausted even when such a determination is in reality premature.

Meanwhile, post-formation of macrostructures on a microtextured laminate may do damage on microtextures such as microprotrusions on the surface of the laminate which may deteriorate surface smoothness or negatively affect fluid transport as embossing sites is embossed at the zero plane of the laminate and is flatted.

Meanwhile, U.S. Pat. No. 5,643,240 discloses a body side liner for absorbent articles comprising an aperture film layer and a separation layer comprising lofty fibrous nonwoven suited for use as a cover material which provides an improved fluid penetration rate, and mitigated rewet by reducing flow-back to the surface of the absorbent article. U.S. Pat. No. 7,695,799 discloses a perforated laminate useful as a topsheet for absorbent articles that comprises first and second layers and perforated apertures that extend through at least the first layer wherein the first layer is a nonwoven that has filaments from about 0.2 to about 15 dpf, or a formed film having a basis weight from about 15 to about 50 gsm, and the second layer comprises a fibrous nonwoven absorbent structure having a median wet pore diameter between about 3 μm and about 50 μm.

Therefore, a need exists for a laminate web providing enhanced fluid drainage and softness.

Therefore, another need exists for a laminate web providing improved masking of stain.

SUMMARY OF THE INVENTION

Disclosed herein is a laminate web comprising a polymer film layer, a nonwoven layer, a first side comprising the polymer film and a second side comprising the nonwoven layer. The laminate web comprises a) a plurality of first elements extending from the polymer film, b) a plurality of second elements which are protrusions extended from the first side of the laminate web, and c) a land area comprising at least one first element which surrounding a majority of the protrusions. Each of the protrusions has a protrusion base in the same plane of the first side of the laminate web, and a majority of the protrusions have no material break such as rupture and tearing of the polymer film between two adjacent first elements at least at the protrusion base.

In addition, disclosed herein is a laminate web comprising a microtextured polymer film layer, a nonwoven layer, a first side comprising the polymer film and a second side comprising the nonwoven layer. The laminate web comprises a) a plurality of first elements extending from the polymer film, b) a plurality of second elements which are recesses downwardly extended from the first side of the laminate web, and c) a land area comprising at least one first element. The recesses may extend below the second side of the laminate web, so that a bottom area of each of the recesses is below the second side of the laminate web.

In addition, disclosed herein is a laminate web comprising a polymer film layer, a nonwoven layer, a first side comprising the polymer film and a second side comprising the nonwoven layer. The laminate web comprises a) a plurality of first elements extending from the polymer film, b) a plurality of second elements, each of the second elements comprising at least one first element, and c) a land area comprising at least one first element and surrounding at least some of the second elements, wherein at least two adjacent second elements, respectively, have one or more than one first element having an open distal end at least 1.5 times larger than the largest distal open end of a first element located in a land between the two adjacent second elements.

In addition, disclosed herein is a laminate web comprising a polymer film layer comprising polymer film, and a nonwoven layer comprising nonwoven web, a first side comprising the polymer film and a second side comprising the nonwoven web, wherein the laminate web further comprises a plurality of first elements, and wherein the nonwoven web comprises a median distance between two adjacent fibers in a z-direction of above about 55 µm.

In addition, disclosed herein is an absorbent article comprising a topsheet comprising the laminate web of the present invention, a liquid impervious backsheet and optionally an absorbent core disposed between the topsheet and the backsheet.

Disclosed herein is also a process for producing the laminate web of the present invention comprising the steps of forming a precursor laminate web comprising a polymeric film layer comprising film and a nonwoven layer, forming a plurality of first elements extending from a first surface of the film layer in the z direction by a vacuum formation process, forming a plurality of second elements, and heat-setting the second elements.

DETAILED DESCRIPTION OF THE INVENTION

Figure 1:
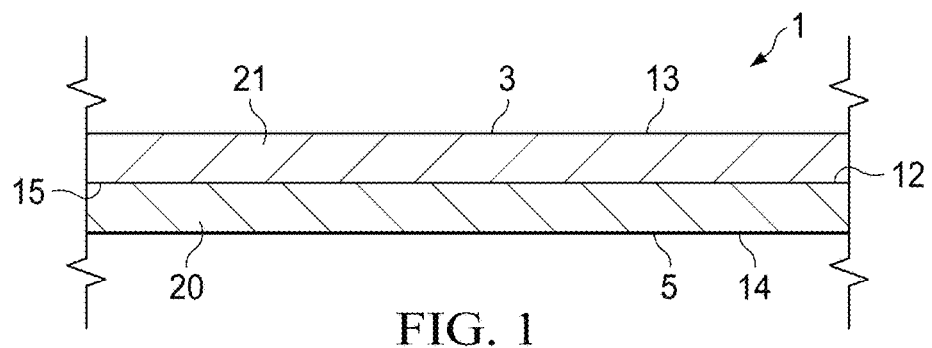
FIG. 1 is a schematic cross section view of a laminate web suitable for the present invention.

The term "absorbent article" includes disposable articles such as sanitary napkins, panty liners, tampons, interlabial devices, wound dressings, diapers, adult incontinence articles, wipes, and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet.

The term "absorbent core", as used herein, refers to the component of the absorbent article that is primarily responsible for storing liquids. As such, the absorbent core typically does not include the topsheet or backsheet of the absorbent article.

The term "adjacent", as used herein, with reference to features or regions, means near or close to, and implies an absence of anything of the same kind in between the features or regions.

The term "aperture", as used herein, refers to a hole. The apertures can either be punched cleanly through the web so that the material surrounding the aperture lies in the same plane as the web prior to the formation of the aperture (a "two dimensional" aperture), or holes formed in which at least some of the material surrounding the opening is pushed out of the plane of the web. In the latter case, the apertures may resemble a protrusion or depression with an aperture therein, and may be referred to herein as a "three dimensional" aperture, a subset of apertures.

The term "component" of an absorbent article, as used herein, refers to an individual constituent of an absorbent article, such as a topsheet, acquisition layer, liquid handling layer, absorbent core or layers of absorbent cores, backsheets, and barriers such as barrier layers and barrier cuffs.

The term "cross-machine direction" or "CD", as used herein, refers to the path that is perpendicular to the machine direction in the plane of the web.

The term "deformable" material, as used herein, is a material which is capable of changing its shape or density in response to applied stresses or strains.

The term "discrete", as used herein, means distinct or unconnected. When the term "discrete" is used relative to forming elements on a forming member such as a roll, plate and belt it is meant that the distal (or radially outwardmost) ends of the forming elements are distinct or unconnected in all directions, including in the machine and cross-machine directions (even though bases of the forming elements may be formed into the same surface of a roll, for example).

The term "forming elements", as used herein, refers to any elements on the surface of a forming member such as a roll, plate and belt that are capable of deforming a web.

The term "layer" used herein should be understood that the term "layer" is not necessarily limited to single layers or sheets of material. Thus, the layer can comprise laminates or combinations of several sheets or webs of the requisite type of materials. Accordingly, the term "layer" includes the terms "layers" and "layered".

The term "machine direction" or "MD", as used herein, refers to the path that material, such as a web, follows through a manufacturing process.

The term "macroscopic" or "macro", as used herein, refers to structural features or elements that are readily visible and distinctly discernable to a human having 20/20 vision when the perpendicular distance between the viewer's eye and the web is about 12 inches (30 cm).

Conversely, the term "microscopic" or "micro" refers to such features that are not readily visible and distinctly discernable under such conditions.

The terms "mechanical deformation", as used herein, refers to processes in which a mechanical force is exerted upon a material to form two-dimensional or three-dimensional structures on a web.

The term "surrounded" or "surrounding", as used herein, refers to both being completely and continuously surrounded, and being discontinuously surrounded by other regions and/or apertures.

Laminate Web

Referring to FIG. 1, a laminate web 1 of the present invention, hereinafter referred to simply as web 1, comprises a nonwoven layer 20 comprising nonwoven web and a polymer film layer 21 comprising polymer film. The nonwoven layer 20 has a first surface 12 and a second surface 14, and film layer 21 has a first surface 13 and a second surface 15. Web 1 has a machine direction (MD) and a cross machine direction (CD) as is commonly known in the art of web manufacturing. The layers are referred to herein as generally planar, two-dimensional webs. The nonwoven layers 20 and the film layer 21 (and any additional layer) can be joined by adhesive, thermal bonding, ultrasonic bonding and the like. Fibrous nonwoven web and film can be joined by applying the nonwoven web onto an extruded film while the film is extruded and still molten, and at least some fibers from the nonwoven web adhering to the molten film. As disclosed below, the constituent layers of web 1 can be joined by interlocking mechanical engagement resulting from the formation of second elements such as protrusions, recesses, embossing, and any combinations thereof.

Web 1 has a first side 3 and a second side 5. The term "sides" is used in the common usage of generally planar two-dimensional webs, such as paper and films that have two sides when in a generally flat condition. In web 1 having elements, two surfaces in a flat land area may be considered the first side and the second side, respectively, that is, a surface in the land area in the film layer side is a first side and a surface in the land area in the nonwoven layer is a second side.

The nonwoven layer and film layer in the laminate of the present invention can have an opacity, and the second elements can be opaque which is preferable for masking of the color of the absorbed fluid. To provide appropriate level of opacity, the nonwoven layer may contain a whitener such as $TiO_2$ no less than 1% by weight of the nonwoven layer. The film layer may contain a whitener such as $TiO_2$ no less than 5% by weight of the film layer. In one embodiment, the film layer contains a higher level of whitener than the nonwoven layer.

Nonwoven Layer

A laminate web of the present invention comprises a nonwoven layer comprising nonwoven web.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaying, and bonded carded web processes, including carded thermal bonding and air-through bonding. The basis weight of nonwoven fabrics is usually expressed in grams per square meter (gsm). The basis weight of the laminate web is the combined basis weight of the constituent layers and any other added components. Fiber diameters are usually expressed in microns (μm); fiber size can also be expressed in denier, which is a unit of weight per length of fiber. The basis weight of laminate webs suitable for use in the present invention can range from 10 gsm to 500 gsm, depending on the ultimate use of the laminate web according to the present invention.

The constituent fibers of the nonwoven web can be comprised of polymers such as polyethylene, polypropylene, polyester, and blends thereof. The fibers can comprise cellulose, rayon, cotton, or other natural materials or blends of polymer and natural materials. The fibers can also comprise a super absorbent material such as polyacrylate or any combination of suitable materials. The fibers can be monocomponent, bicomponent, and/or biconstituent, non-round (e.g., protrusionillary channel fibers), and can have major cross-sectional dimensions (e.g., diameter for round fibers) ranging from 0.1-500 μm. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. protrusionillary and round) and the like. The constituent fibers can range from about 0.1 denier to about 400 denier.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "non-round fibers" describes fibers having a non-round cross-section, and includes "shaped fibers" and "protrusionillary channel fibers." Such fibers can be solid or hollow, and they can be tri-lobal, delta-shaped, and are preferably fibers having protrusionillary channels on their outer surfaces. The protrusionillary channels can be of various cross-sectional shapes such as "U-shaped", "H-shaped", "C-shaped" and "V-shaped".

A nonwoven layer may comprise fibers having sufficient elongation properties to have portions elongated. The portion elongated are formed by urging fibers out-of-plane in the Z-direction at discrete, localized, portions of the nonwoven layer. The urging out-of-plane can be due to fiber displacement, i.e., the fibers are able to move relative to other fibers and be "pulled," so to speak, out-of-plane. More often, however, for most nonwoven layers suitable for the laminate according to the present invention, the urging out-of-plane is due to the fibers having been at least partially plastically stretched and permanently deformed.

The nonwoven layer useful for the laminate web according to the present invention can comprise a nonwoven web comprised of substantially randomly oriented fibers. By "substantially randomly oriented" is meant that, due to processing conditions for producing the precursor nonwoven web, there may be a higher amount of fibers oriented in the MD than the CD, or vice-versa.

The nonwoven layer may have a basis weight of between and about 60 gsm, between about 12 gsm and about 25 gsm, or between about 12 gsm and about 18 gsm. In general, nonwoven, especially spunbond nonwoven, of higher basis weight reduces an acquisition speed though it may increase stain masking.

In one embodiment of the present invention, the nonwoven layer comprises a median distance between two adjacent fibers in a z-direction of above about 55 μm, or in the range of about 60 to about 200 μm, when measured according to the Fiber-Fiber Distance Measurement described in the present specification. When the nonwoven layer comprises carded nonwoven, the carded nonwoven can be produced to have a median distance between two adjacent fibers in a z-direction of above about 55 μm by optimizing production conditions such as oven air flow temperature, hot air pressure, and nonwoven web tension when the web goes through the oven and/or calendar rolls in order to increase a caliper of the nonwoven. For example, the higher oven air flow temperature, the lower caliper of the nonwoven, and the higher hot air pressure, the lower caliper for the nonwoven. In addition, a tighter web tension may result in a lower caliper of the nonwoven. In one example, the nonwoven web is carded nonwoven formed from a polymer having a fiber thickness of no less than 5 denier.

Film Layer

A laminate web of the present invention comprises a film layer comprising polymer film. The polymer film comprises a plurality of first elements.

Polymer film having first elements can be provided using any process known in the art. Polymer film with first elements will provide the exterior surfaces of the web with a softer, more cloth-like texture, provide the web with a more cloth-like appearance, and increase the overall caliper of the web. Examples of process forming first elements include but are not limited to the following: mechanical deformation, flocking, ultrasonics, delamination of viscous melts from porous surfaces, brushing, and any combination thereof.

The film layer may have a basis weight of between about 8 gsm to about 35 gsm, between about 10 gsm to about 20 gsm, or between about 10 gsm to about 14 gsm. Or, the film layer may have a basis weight of between about 8 gsm to about 20 gsm, between about 10 gsm to about 18 gsm, or between about 12 gsm to about 15 gsm. If the second precursor web has a basis weight more than 20 gsm, desirable softness of laminates may not be obtained. If the film has a basis weight less than 8 gsm, it may tear during wearing of absorbent articles having the laminate of the present invention.

The film layer may have sufficient integrity to be formed into the laminate web by the process especially when the laminate web has second elements in addition to first elements. It may have sufficiently high elongation properties such as stretchability relative to nonwoven layer at a process temperature, especially at the temperature in a protrusion forming step described in detail below, such that upon experiencing the strain of fibers from the nonwoven layer being urged out-of-plane in the direction of the film layer, the film layer does not break or rupture, e.g., by tearing due to extensional failure, so that a majority of the second elements have no material break between two adjacent first elements described in detail below.

First Elements

The laminate web according to the present invention comprises a plurality of first elements extending from the polymer film. The first elements may have open proximal ends, open or closed distal ends, and sidewalls. The first elements may extend outwardly from the first side of the laminate web. Without being bound by theory, it is believed the first elements extended upwardly from the polymer film provide softness and overall comfort to the skin when a film layer from which the first elements extend is skin-facing layer in absorbent articles as it may limit the film with protrusions directly contact the skin.

The first elements provide microtexture to the laminate web. The first elements can, for example, be microapertures or micro bubbles, examples of which are disclosed in U.S. Pat. No. 7,454,732, issued to Stone et al. and U.S. Pat. No. 4,839,216 issued to Curro et al., U.S. Pat. No. 4,609,518 issued to Curro et al. As an example, the first elements can be micro-apertures, the apertures have an area of between about 0.01 mm$^2$ and about 0.78 mm$^2$.

The first elements can also be aperutred protrusions, non-apertured protrusions or fibrils to provide texture that provides for a tactile impression of softness. Softness is beneficial when webs are used as topsheets in disposable absorbent articles. Referring to FIGS. 13A, 14A-14D and 17A-17D, the web 1 according to the present invention is effective in preserving first elements 4 even when the second elements 7 are formed on precursor webs having the first elements 4.

In one embodiment, the first elements are discrete extended elements having a diameter shorter than a minor axis of protrusions formed in the web of the present invention. In one non-limiting embodiment, the discrete extended elements have a diameter of less than about 500 microns; the discrete extended elements have an aspect ratio of at least about 0.2; and/or the web comprises at least about 95 discrete extended elements per square centimeter. References disclosing such a plurality of discrete extended elements include WO 01/76842; WO 10/104996; WO 10/105122; WO 10/105124 and US20120277701A1.

In embodiments when the first elements are discrete extended elements with open ends, the discrete extended elements may be formed by applying high pressure vacuum against the forming surface of the forming member that the formed web ply is against. Such methods of aperturing are known as "Vacuum Forming" and are described in greater detail in U.S. Pat. No. 4,463,045. Examples of mechanical deformation is disclosed in U.S. Pat. Nos. 4,798,604, 4,780, 352, 3,566,726, 4,634,440, WO 97/40793, and European Patent 525,676. Examples of flocking are disclosed in WO 98/42289, WO 98/36721, and European Patent 861,646. Examples of ultrasonics are disclosed in U.S. Pat. No. 5,269,981. Examples of delamination of viscous melts are disclosed in U.S. Pat. No. 3,967,623, and WO 99/06623. Examples of printed hair are disclosed in U.S. Pat. No. 5,670,110. Examples of brushing are disclosed in WO 99/06623.

Second Elements

A laminate web according to the present invention may comprise a plurality of second elements. The second elements are macro features, and may be selected from the group consisting of protrusions, embosses, recesses, apertures and combinations thereof. The second element preferably comprises an arched side wall. The second element be a macroscopic structure.

Second elements are discrete, and may be of any suitable configuration. Suitable configurations for second elements include, but are not limited to, features having plan view configurations including circular, oval, hour-glass shaped, star shaped, polygonal and the like, and combinations thereof. "Polygonal" herein intends to include polygonal with rounded corners. Polygonal shapes include, but are not limited to triangular, quadrilateral, hexagonal, octagonal or trapezoidal. The second elements may be arranged in a staggered pattern. In one embodiment, the second elements have a plan view substantially quadrilateral such as rectangular, square, and lozenge shape. Lozenge shaped second elements are preferred in a staggered array as the shapes can be well nested and minimize land area 8 between adjacent second elements.

The second elements may have a major axis and a minor axis perpendicular to the major axis. In one embodiment, the major axis of the second elements is substantially parallel to the MD of a laminate web 1 of the present invention. In another embodiment, the major axis of the second elements is substantially parallel to the CD of the web 1. In another embodiment, the major axis of the second elements is oriented at an angle relative to the MD of the web 1. Despite the terms of 'major" and "minor" axes, it is intended that a major axis and a minor axis can have an identical length.

The plan view area of an individual second element, in some embodiments of the laminate web of the present invention, may be greater than or equal to about $0.25 \text{ mm}^2$, $0.5 \text{ mm}^2$, $1 \text{ mm}^2$, $5 \text{ mm}^2$, $10 \text{ mm}^2$, or $15 \text{ mm}^2$. The number of second elements per unit area of the laminate web of the present invention, i.e., the density of second elements, can be varied from about 5-60 second elements/$\text{cm}^2$. In one embodiment, the laminate web may comprise second elements with a second element density of from about 5 to about 60, or from about 10 to about 50, or from about 20 to about 40 second elements/$\text{cm}^2$ web. There can be at least 20 second elements/$\text{cm}^2$ web, depending on the end use of the web. In general, the second element density need not be uniform across the entire area of the laminate web of the present invention, but the second elements can be only in certain regions of the web, such as in regions having predetermined shapes.

The extension of polymer film in the second elements can be accompanied by stretch of the film and a general reduction in thickness of the film. The stretch and reduction in thickness of the film may result in improvement of fluid handling as open distal ends of the first elements are enlarged, and improvement of softness as thinned film has reduced modulus properties which provide the perception of softness to the users when touching the laminate web.

Figure 2A:
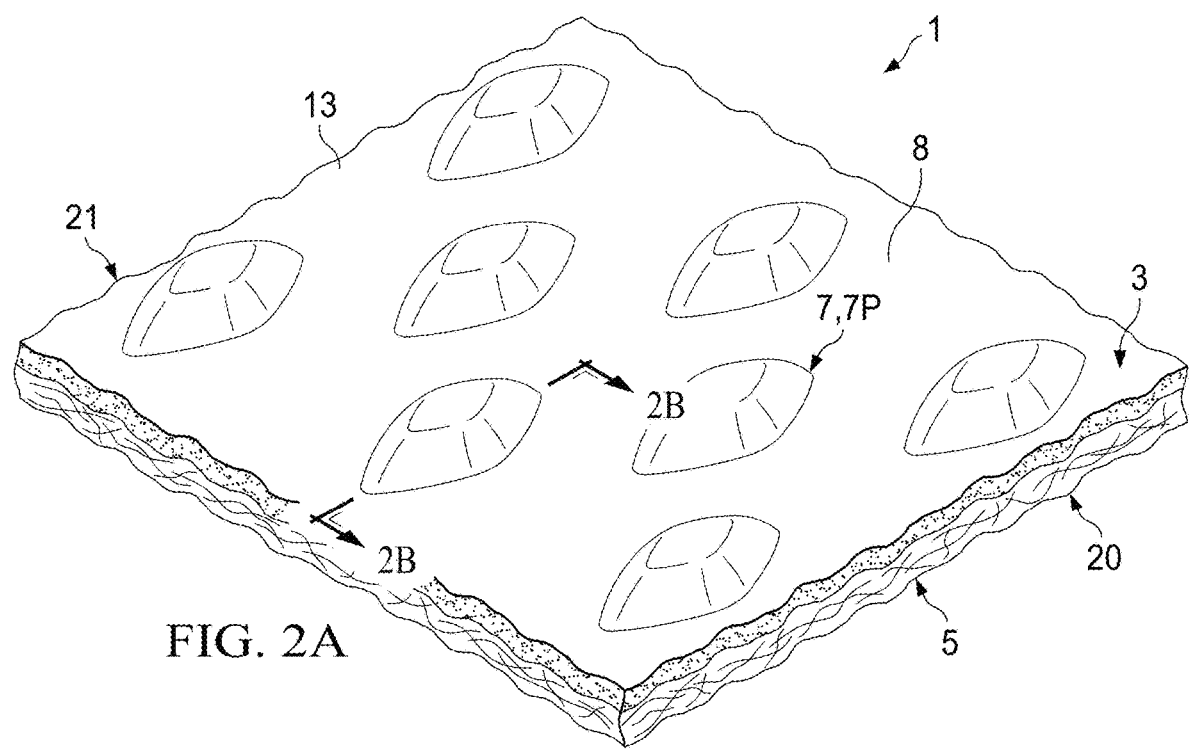
FIG. 2A is a schematic perspective view of a laminate web having protrusions according to the present invention.
Figure 2B:
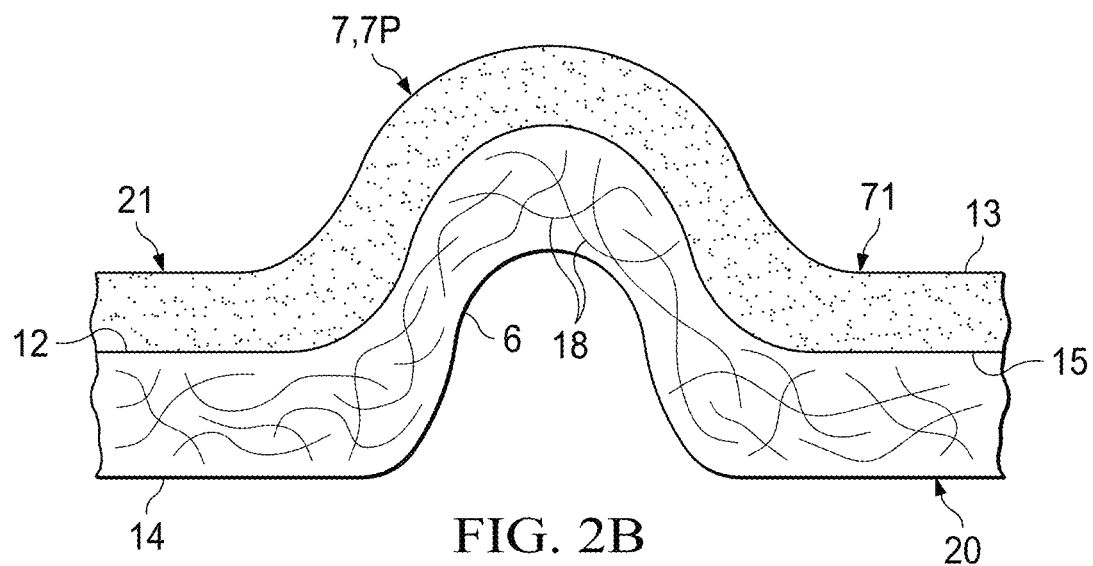
FIG. 2B is an enlarged cross-sectional view of section 2A-2A of FIG. 2A.
Figure 4A:
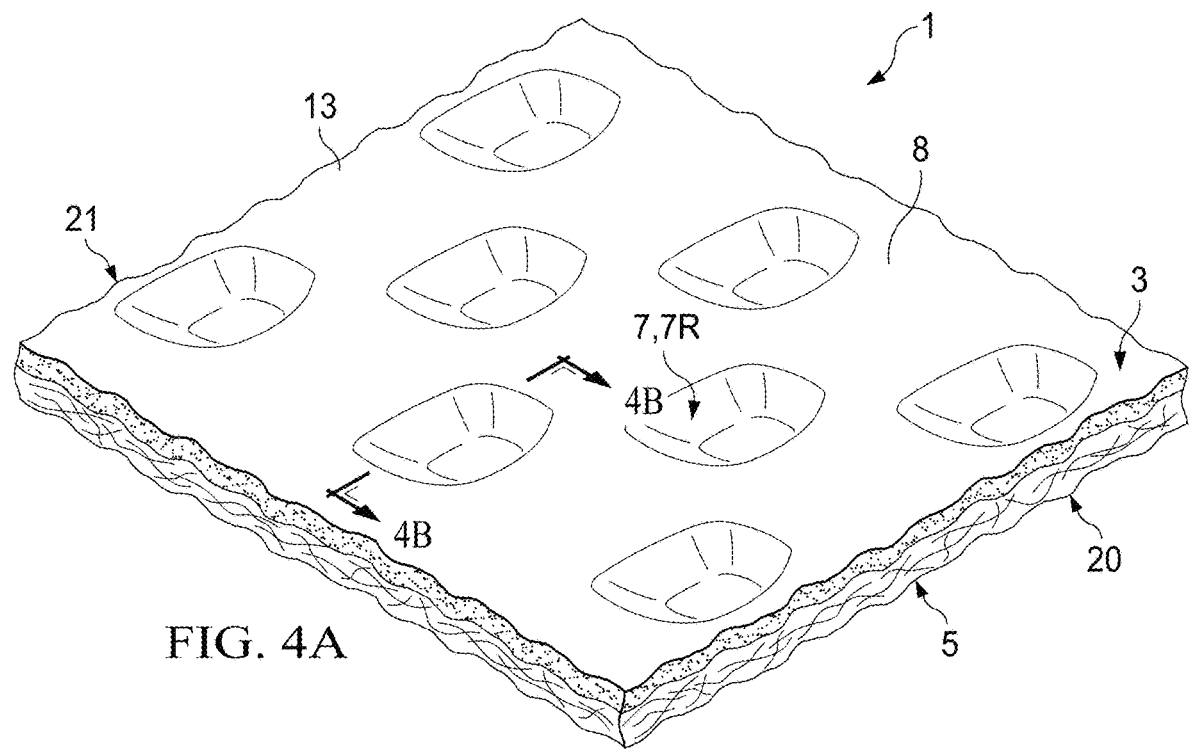
FIG. 4A is a schematic perspective view of a laminate web having recesses according to the present invention.
Figure 4B:
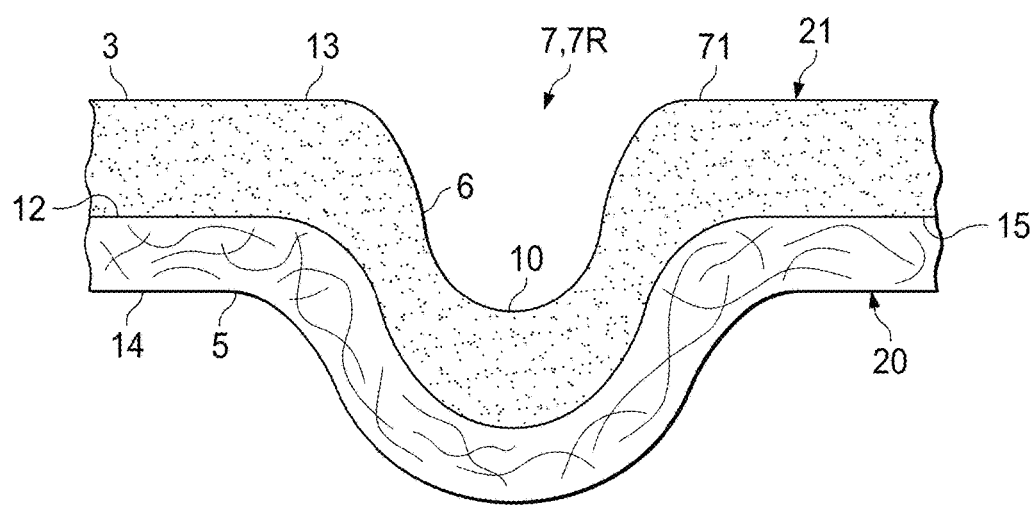
FIG. 4B is an enlarged cross-sectional view of section 4B-4B of FIG. 4A.

Referring to FIGS. 2A and 2B showing second elements 7, protrusions 7P in this case, and FIGS. 4A and 4B showing second elements 7, recesses 7R in this case, second elements 7 may be integral extensions of the polymer film 21. As used herein, the term "integral" as in "integral extension" when used for second elements such as protrusions and recesses refers to the substrate forming the protrusion having originated from the polymer film. Therefore, the second element can be a plastically deformed elongated substrate of the polymer film, and is, therefore, integral with the polymer film.

Figure 3:
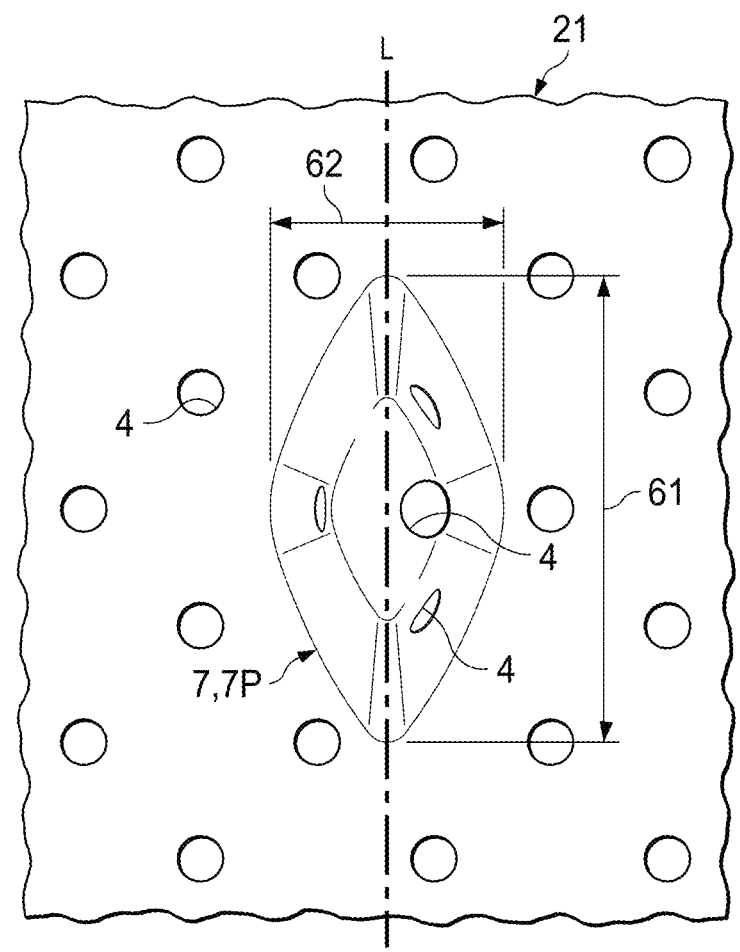
FIG. 3 is a plan view of an enlarged portion of the laminate web having a protrusion shown in FIG. 2A.

Referring to FIG. 3, second element 7 can have a length and a width. The length of second element 7 is a length in a major axis of the second element 7. Second element 7 can also have a width taken to be the maximum dimension of the second element 7 as measured orthogonal to the length 61 of the second element 7.

Referring to FIGS. 2B and 4B, the second element 7 can have a base 71 in the same plane of the first side of the laminate web 1. The second element 7 integrally extends from the base 71. The base 71 can be wider than a vertical cross section of the second element 7 away from the base 71. That is, a width or a length of the base 71 can be longer than a width or a length in a cross-section of the second element 7 away (i.e. above or below) from the base 71.

Second elements 7 in the web 1 may enhance fluid drainage. Without being bound by theory, it is believed that fluid drainage may be improved via the arching or sloped side wall in the second elements and a very small area of plateau on the top (when the second elements are protrusions) or the bottom area 10 (when the second elements are recesses or embosses) in the 3-dimensional structure of the second element 7.

Enhanced drainage may result in reducing perceivable stain on the top side of absorbent article product having a topsheet comprising the laminate web of the present invention. Stain reduction may help users avoid determining to prematurely replace absorbent article products. Moreover, it provides perceived clean and dry topsheet as well as perceived good absorbent performance.

If the polymer film comprises a whitener such as titanium dioxide, the second elements 7 can be more effective at obscuring materials. Such second elements 7 can better maintain a perceived color of white, which many consumers associate with cleanliness.

Polymer film layer 21 can have a polymer film thickness t and the second element 7 can have a second element thickness pt. Being that the second elements 7 are integral extensions of the polymer film layer 21 and formed by stretching the polymer film out of plane of the first side 3 of the web 1, the second element thickness pt of a portion of the second element 7 can be less than the polymer film thickness t. That is, the polymer film that is elongated to form a second element 7 is thinned at least some portion of the second element 7 relative to the planar portion of the polymer film from which the second element 7 extends. The second element thickness pt at a distal portion of the second element 7 may be about the same or less than the polymer film thickness t and the second element thickness pt at a portion of the second element 7 between the distal portion of the second element 7 and the polymer film may be less than the polymer film thickness t. Thinning of the second element 7 may provide for second element 7 having a soft feel to the skin. Second element 7, as the polymer film is stretched, has at least one first element having an enlarged open distal end which results in faster fluid acquisition. By stating of one first element having an enlarged open distal end, it intends to mean that the first element has an open distal end which is larger than an original open distal end.

Second elements 7 may not have break or rupture, e.g., by tearing due to extensional failure of the polymer film, so that majority of second elements 7 may have no material break between two adjacent first elements, especially in a base 71.

The first and/or second precursor webs can have an opacity, and the second elements can be opaque which is preferable for masking of the color of the absorbed fluid. To provide appropriate level of opacity, the nonwoven layer 20 may contain a whitener such as $TiO_2$ no less than 1% by weight of the nonwoven layer 20. The polymer film layer 21 may contain a whitener such as $TiO_2$ no less than 5% by weight of the polymer layer 21. In one embodiment, the polymer film layer 21 contains a higher level of whitener than the nonwoven layer 20.

The second element 7 comprises one or more than one first element 4. At least some of the second elements may have first elements having stretched and enlarged distal open ends.

In some embodiments, at least one first element 4 in the second elements 7 has an open distal end larger than at least one first element 4 in an adjacent land area 8. As used herein, the term an "adjacent land area" refers to a land area located between two adjacent recesses. Therefore, by stating that at least one first element 4 in the second element 7 has an open distal end larger than at least one first element 4 in an adjacent land area 8, it intends to mean that at least one first element 4 in one second element 7 has an open distal end larger than at least one first element 4 in a land area located between the second element 7 and another second element 7 adjacent to the second element 7. Referring to FIGS. 13A, 14A-14D, and 17A-17D, the web 1 of the present invention may comprise at least two adjacent second elements 7, respectively, have at least one first element having an open distal end at least 1.5 times, or at least 2 times, or at least 3 times larger than the largest distal open end of a first element located in a land between the two adjacent second elements. In one embodiment, the web of the present invention comprises at least three adjacent second elements, respectively, have at least one first element having an open distal end at least 1.5 times larger than the largest distal open end of a first element in a land surrounded the adjacent three second elements. In another embodiment, the web of the present invention comprises at least four adjacent second elements, respectively, have at least one first element having an open distal end at least 1.5 times larger than the largest distal open end of a first element in a land surrounded the adjacent four second elements.

Protrusions

Referring to FIGS. 2A and 2B, in some embodiments, the second elements are protrusions 7P. The second element 7, a protrusion 7P in this case, has a base 71 in the same plane of the first side 3 of web 1. Referring to FIGS. 13A and 14A-14D, formation of protrusions 7P as second elements 7 may have a stretched and enlarged open end of the first elements 4 on the second element 7 which enables faster fluid acquisition as it may make more fibers from the nonwoven contact in direct with the fluid.

Protrusion 7P in the web 1 may also be better in stain masking. Fibers originated from the nonwoven layer 20 where fluid collected by the laminate web 1 may be held are not exposed above protrusion 7P which can make the web 1 appear less red.

In some embodiments, as described below, another characteristic of protrusion 7P may be their generally open structure characterized by void area defined interiorly of protrusion 7P, as shown in FIG. 2B. By "void area" is not meant an area completely free of any fibers; the term is meant as a general description of the general appearance of protrusion 7P. Therefore, it may be that in some protrusion 7P at least one fibers elongated from the nonwoven layer 20 may be present in the void area. From the description of web 1 comprising a nonwoven layer 20, in general, elongated portions 6 comprises fibers 18 that extend from the nonwoven layer 20. Elongated portions 6 are not extended above the protrusion 7P.

Protrusion 7P does not have break or rupture, e.g., by tearing due to extensional failure of the polymer film, so that majority of protrusion 7P have no material break between two adjacent first elements, especially in a protrusion base 71. By stating that majority of protrusions have no material break between two adjacent first elements, it intends to mean that at least more than 60% of protrusions per 1 cm$^2$ laminate web have no material break between two adjacent first elements.

Recesses

Referring to FIGS. 4A and 4B, in other embodiments, the second elements 7 are recesses 7R formed inwardly from the first side of the web 1 toward the second side of the web 1. A bottom area 10 of the recess 7R may be below the second side 5 of the web 1. The bottom area 10 may comprises a plateau area. In some embodiments, the bottom area 10 of the recess 7R is from about 0.05 mm$^2$ to about 15 mm$^2$, or from about 0.1 mm$^2$ to about 3 mm$^2$. The bottom area 10 may be downwardly concaved so that there is a very small area of plateau which can prevent the fluid to be trapped between first elements in the bottom area 10. In such embodiments, referring to FIGS. 15A-17D, recesses 7R may extend below the second side 5 of the web 1, so that a bottom area 10 of the recess 7R is below the second side 5 of the web 1. In some examples, recesses 7R may extend at least about 50 μm below the second side 5 of the web 1.

Figure 15A:
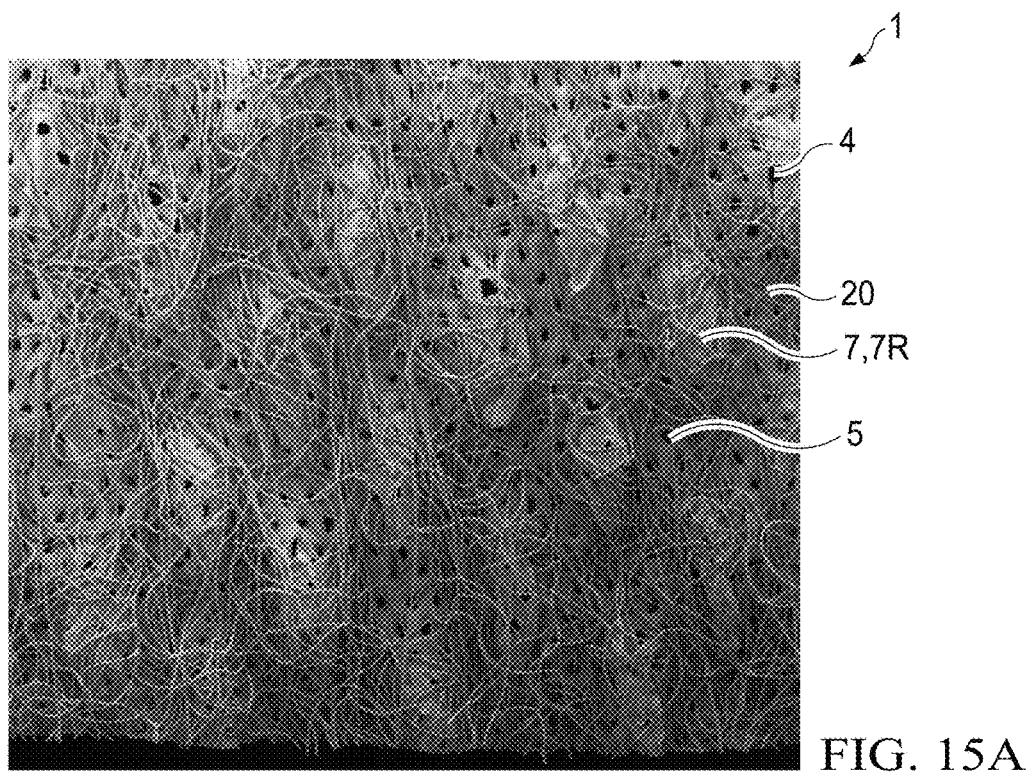
FIG. 15A is a plan view of a nonwoven side scanning electron microscope image of a laminate web having recesses according to the present invention.
Figure 16:
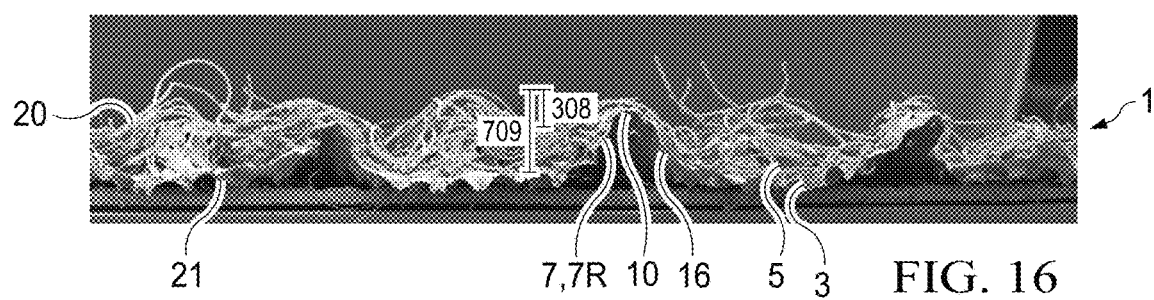
FIG. 16 is a plan view of a microscopic image of a cross section in the width direction of recesses of the laminate web of FIG. 15A.

Referring to FIGS. 15A and 16, in one embodiment of the present invention, formation of recesses 7R makes the land area have sloped and arched edges due to the specifically designed teeth as explained in detail later. The sloped arch formation on the land area between the recesses also helps fluid drain out of valleys between the first elements 4. Additionally, extension of polymer film in the recesses 7R can be accompanied by stretch of the film and a general reduction in thickness of the film. The stretch and reduction in thickness of the film may result in improvement of fluid handling as open ends of the first elements 4 can be enlarged. The enlarged open ends in the first elements 4 help more fibers from the nonwoven contact directly with the fluid.

In addition, as shown in FIGS. 16A and 17A-17D, the first elements 4 located in macro structures, recesses 7R in this case, which may be damaged during formation of the macro structures, are not exposed on or above either side of the web 1, therefore softness of a surface of the web 1 is not deteriorated.

Apertures

Figure 19:
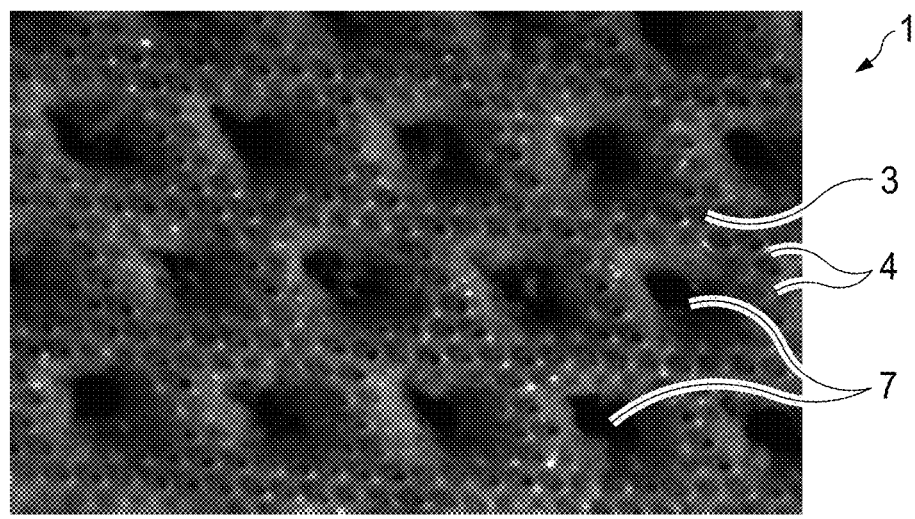
FIG. 19 is a microscopic image in a film side of a laminate web of another embodiment according to the present invention.

Referring to FIG. 19, in other embodiments, the second elements 7 may be apertures. The apertures may be formed inwardly from the first side 3 of the web toward the second side of the web 1.

Land Area

The laminate web according to the present invention comprises a land area which surrounds the second elements. Referring to FIGS. 15A-15D and 17A-17D, the land area 8 comprises at least one first element 4, or at least two first elements 4.

Third Elements

The laminate web according to the present invention optionally comprises a plurality of third elements. The third elements are macro features, and may be selected from the group consisting of apertures, embosses, recesses and a combination thereof. The third elements may be planar and two dimensional or three dimensional. "Planar" and "two dimensional" is meant simply that the web is flat relative to the web 1 that has distinct, out-of-plane, Z-direction three-dimensionality due to the formation of the third elements. "Planar" and "two-dimensional" are not meant to imply any particular flatness, smoothness or dimensionality. Each of the third elements may be formed between two adjacent second elements. Descriptions provided with respect to a size and density of the second elements are applicable for the third elements.

In one embodiment where the laminate web of the present invention used as a topsheet in an absorbent article such as a sanitary napkin, the third elements can be only in the region corresponding to the central part of the article where fluid entry occurs.

Apparatus and Method for Manufacturing Laminate Web

The first elements 4 and optionally second elements 7 in web 1 can be formed using any processes known in the art. Examples of such processes include but are not limited to the following: vacuum forming, mechanical deformation, ultrasonics, slitting, ring-rolling, and any combination thereof.

Methods for vacuum formation, mechanical deformation, and ultrasonics are described above. With respect to ultrasonics, additional methods are disclosed in U.S. Pat. Nos. 5,269,981 and 5,269,981. Suitable slitting methods are disclosed in PCT Publication WO 97/31601. In one embodiment, the second elements of the present invention may be formed by a mechanical deformation process. The mechanical deformation process can be carried out on any suitable apparatus that may comprise any suitable type(s) of forming structure. Suitable types of forming structures include, but are not limited to: a pair of rolls that define a nip therebetween; pairs of plates; belts, etc. Using an apparatus with rolls can be beneficial in the case of continuous processes, particularly those in which the speed of the process is of interest. Although the apparatuses will be described herein for convenience primarily in terms of rolls, it should be understood that the description will be applicable to forming structures comprising a forming member that have any other suitable configurations.

The rolls for a mechanical deformation process forming first elements and/or second elements, and optionally the third elements described herein are typically generally cylindrical. The term "generally cylindrical", as used herein, encompasses rolls that are not only perfectly cylindrical, but also cylindrical rolls that may have elements on their surface. The term "generally cylindrical" also includes rolls that may have a step-down in diameter, such as on the surface of the roll near the ends of the roll. The rolls are also typically rigid (that is, substantially non-deformable). The term "substantially non-deformable", as used herein, refers to rolls having surfaces (and any elements thereon) that typically do not deform or compress under the conditions used in carrying out the processes described herein. The rolls can be made from any suitable materials including, but not limited to steel, aluminum or rigid plastic. The steel may be made of corrosion resistant and wear resistant steel, such as stainless steel. At least one of the rolls may or be heated. If heated, consideration of thermal expansion effects must be accommodated according to well known practices to one skilled in the art of thermo-mechanical processes.

The rolls for a mechanical deformation process forming second elements 7, and optionally the third elements described herein have surfaces which may be provided with forming elements comprising: male elements such as discrete projections such as teeth; female elements such as recesses such as discrete voids in the surface of the rolls; or any suitable combination thereof. The female elements may have a bottom surface (which may be referred to as depressions, or cavities), or they may be in the form of apertures (through holes in the surface of the rolls). In some embodiments, the forming elements on the members such as the rolls of the forming unit may comprise the same general type (that is, the opposing components may both have forming elements thereon, or combinations of forming and mating elements). The forming elements may have any suitable configuration. One type of male elements useful in the present invention are teeth having a base in a generally polygonal shape such as octagonal, hexagonal and quadrilateral shape, and having a cross-sectional length and a cross-sectional width. The teeth have any suitable aspect ratio of its cross-sectional length to its cross-sectional width to form macroscopic structures, in a web. In one embodiment, the teeth have a generally hexagonal shape base. In another embodiment, the teeth have a generally quadrilateral shape base.

The male elements can have tips that are flat, rounded or sharp. In certain embodiments, the shapes of the female elements may differ from the shapes of any mating male elements. In certain embodiments, the female elements can be configured to mate with one or more male elements.

Figure 5:
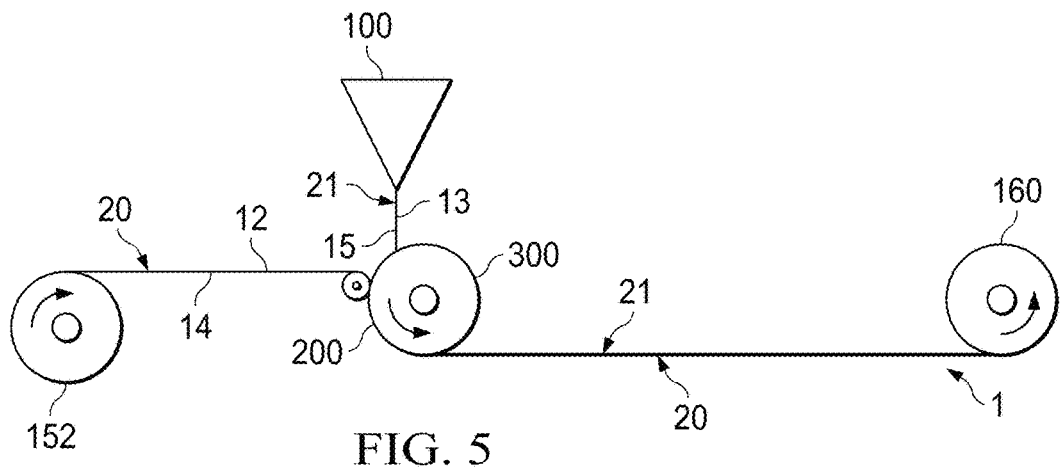
FIG. 5 is a schematic representation of a process for forming a laminate web of the present invention.

A laminate of one embodiment of the present invention may be produced by laminating a nonwoven web (layer) and a polymer film to obtain a precursor laminate web, and forming the first elements. Alternatively, a laminate web of the present invention may be produced by laminating a nonwoven web (layer) and a polymer film having a plurality of first elements. The nonwoven web (layer) and the polymer film may be provided either directly from their respective web making processes or indirectly from supply rolls and moved in the machine direction to the laminating process. Referring to FIG. 5, an exemplary process for producing one embodiment laminate web 1 comprises a step of laminating a nonwoven layer 20 and a polymer film layer 21 and a step of forming a plurality of first elements in first element forming unit 200.

Figure 6A:
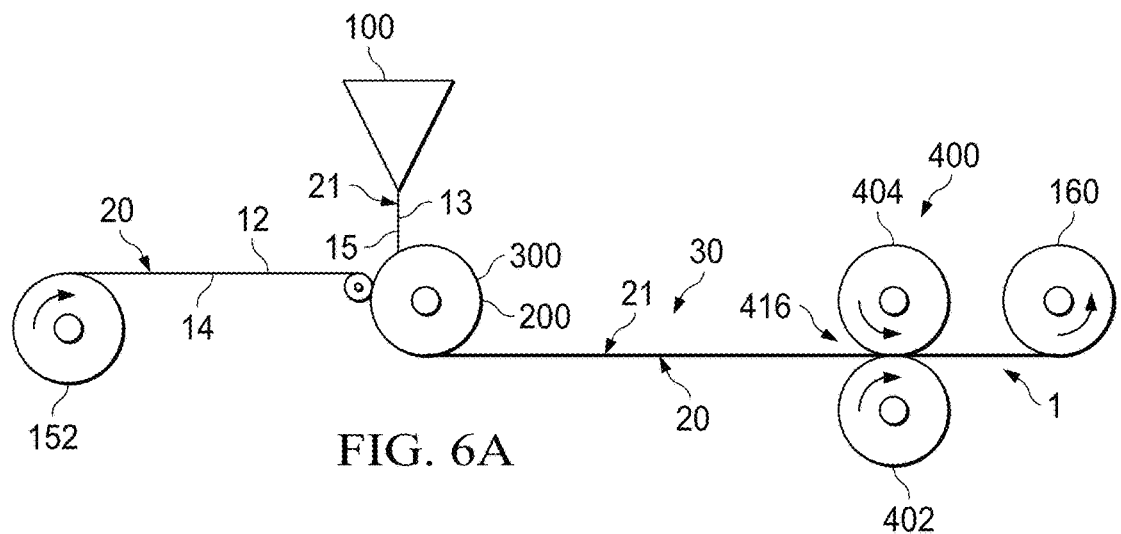
FIG. 6A is a schematic representation of a process for forming another laminate web of the present invention.
Figure 6B:
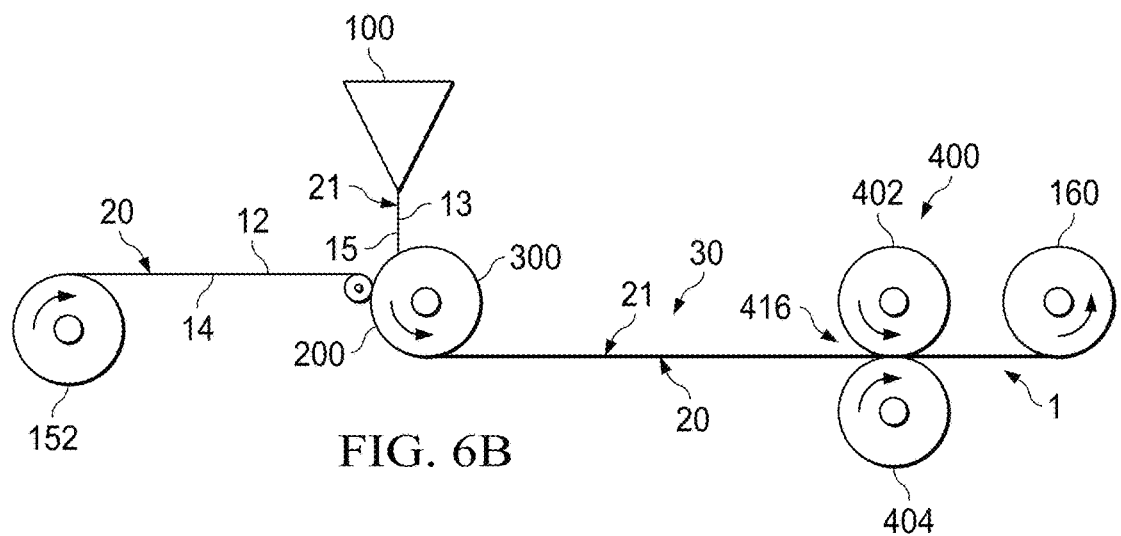
FIG. 6B is a schematic representation of a process for forming another laminate web of the present invention.

A laminate web of another embodiment of the present invention having first elements and second elements can be produced by laminating a nonwoven web (layer) and a polymer film having a plurality of first elements to obtain a precursor laminate web, and mechanically deforming the precursor laminate web. The nonwoven web (layer) and the polymer film are provided either directly from their respective web making processes or indirectly from supply rolls and moved in the machine direction to the first elements and second elements forming process. The laminate web can be produced by a continuous process comprising a step of forming a plurality of first elements in a precursor film layer and a step of forming a plurality of second elements via a second element forming unit. The web also can be produced mechanically deforming a polymer film having a plurality of first elements. Referring to FIGS. 6A and 6B, exemplary processes for producing web 1 comprise a step of forming a plurality of first elements in first element forming unit 200 and a step of forming a plurality of second elements in second element forming unit 400. The laminate web can also be produced by laminating a nonwoven 20 and a polymer film 21 having a plurality of first elements to obtain a precursor laminate web, and mechanically deforming the precursor laminate web.

In embodiments illustrated in FIGS. 6A and 6B, second precursor web 21 is produced and supplied directly from a film making apparatus such as a polymer film extruder 100 which extrudes a molten film which is to be a polymer film layer 21. FIG. 6A is a schematic representation of a process for forming a laminate web of the present invention having a plurality of second elements extended outwardly from a film layer side of the laminate web such as protrusions. FIG. 6B is a schematic representation of a process for forming a laminate web of the present invention having a plurality of second elements extended inwardly from a film layer side toward a nonwoven layer side of the laminate web such as recesses and embosses. The extruded polymer film 21 is continuously moved to first element forming unit 200. Nonwoven 20 is unwound from the supply roll 152 and is applied on the second precursor web in the first element forming unit 200 so that the first surface 12 of the nonwoven 20 is faced with the second surface 15 of the polymer film 21. When the first and second precursor webs are laminated on a roll 300, using an idler, nonwoven layer 20 is pressed slightly against the polymer film 21 while the polymer film 21 is still molten so that fibers of the nonwoven 20 can slightly penetrate into the polymer film 21 and the nonwoven and polymer film are bonded to each other and form precursor laminate web 30. The first element forming unit 200 comprises, for example on its surface, a vacuum forming slots to form the first elements. The precursor laminate web 30 comes into contact with the forming slots through which a strong vacuum is created. The first elements are formed substantially only on the film layer 21 as the nonwoven layer 20 is porous and does not interfere with the formation of the first elements on nonwoven 21. The precursor laminate web 30 having the first elements is moved in the machine direction by means known in the art, including over or around any of various idler rolls, tension-control rolls, and the like (all of which are not shown) to second element forming unit 400. As an example, the second element forming unit comprises a pair of counter-rotating, intermeshing rolls 402 and 404 wherein the first roll 402 comprises a plurality of first male elements such as teeth, and the second roll 404 comprises a plurality of first female elements. Subsequent to the second element formation, the web 1 can be taken up on a supply roll 160 for storage and optionally for further processing as a component in other products. Alternatively, the web 1 can be conveyed directly to further post processing, including a converting operation for incorporation into a finished product, such as a disposable absorbent product.

In another exemplary process, second precursor web 21 is produced in line, and deformed to have a plurality of first element before being laminated with first precursor web 20. The second precursor web 21 deformed to have first elements may be laminated with first precursor web 20 using adhesive or thermal bonding process.

In another exemplary process, polymer film 21 may be a formed film having a plurality of first elements pre-formed. The polymer film 21 is supplied from a separate supply roll and the nonwoven 20 is supplied onto the second surface 15 of the polymer film 21 to form precursor laminate web 30. Since the polymer film 21 already has the first elements, the precursor laminate web 30 is directly supplied to a second element formation unit without undergoing the first element formation step.

Figure 7:
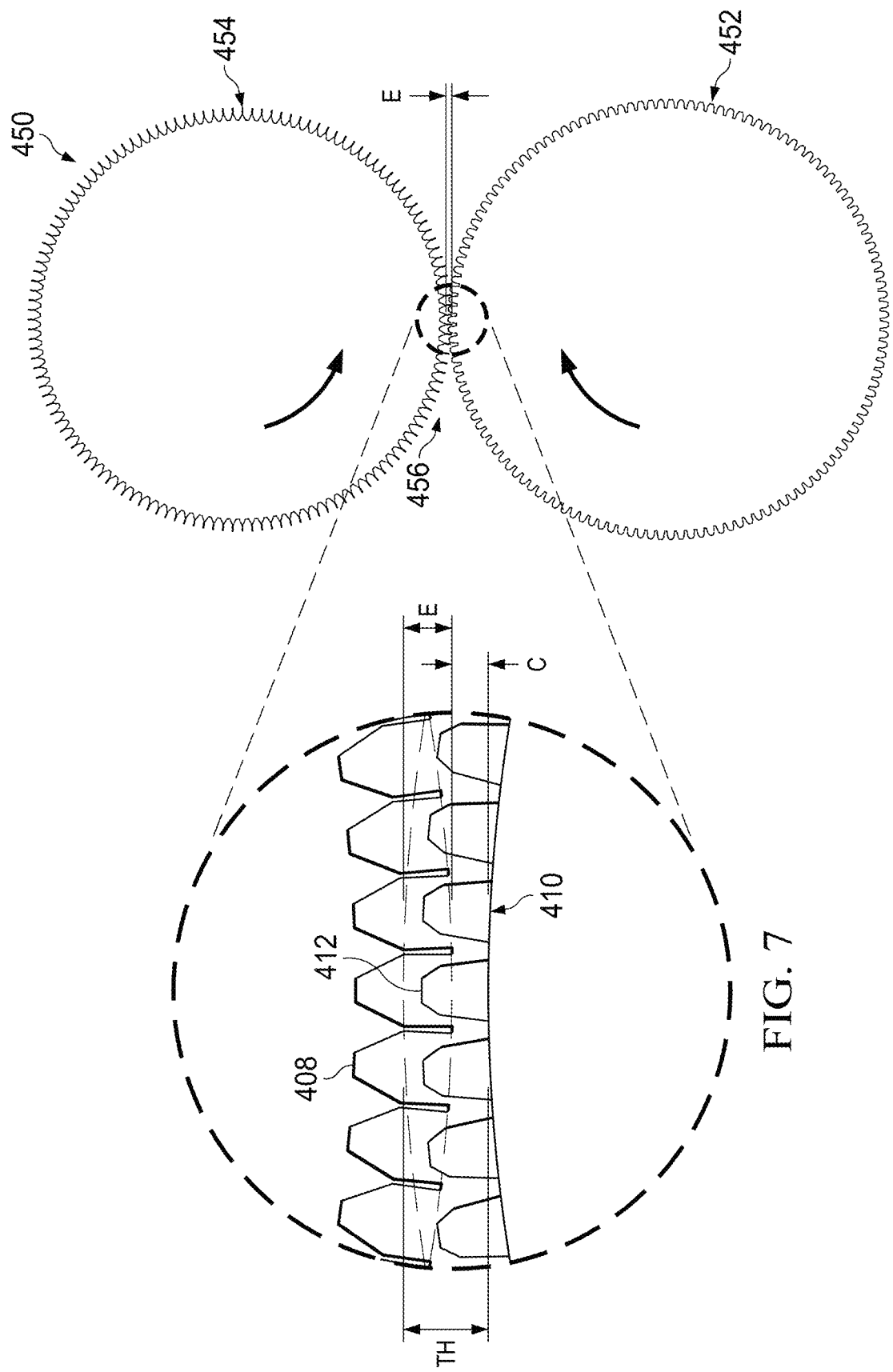
FIG. 7 is a cross-sectional representation of a portion of a second element forming unit forming a laminate web of the present invention.

FIG. 7 shows in more detail the portion of an exemplary second element forming unit 450 for a second element forming step to form second elements 7 in precursor laminate web 30. Second element forming unit 450 comprises a pair of intermeshing rolls 452 and 454 rotating in opposite directions. Second element forming unit 450 can be designed such that precursor laminate web 30 remains on roll 452 through a certain angle of rotation. The second element forming step may be carried out in a process speed not causing ruptures or tearing in the second elements. The process speed may be determined considering stretchability of the film at the process temperature. While FIGS. 6A, 6B and 7 show precursor laminate web 30 going straight into and web 1 coming straight out of the nip 416, 456 formed by a pair of rolls of second element forming unit 400, 450, precursor laminate web 30 or web 1 can be partially wrapped on either of first roll 402, 452 or second roll 402, 454 through a predetermined angle of rotation prior to (for precursor laminate web 30) or after (for web 1) the nip. For example, after exiting nip 456, web 1 can be directed to be wrapped on roll 452 through a predetermined angle of rotation such that the second elements remain resting over, and "fitted" onto, teeth 410 of roll 452. The second elements having first elements with enlarged open ends may be stabilized by heat-setting them film layer of web 1 during the second element forming step. Web 1, when it comes out of the nip 416, 456, specifically, the film layer is heat-set to the shape of the second elements so that the film layer does not recover back to its original shape such as a flat sheet or close to the original shape. The heat-set may be conducted by resting over the web 1 on teeth 410 of heated roll 452 at or near the softening point of film of the film layer. The heat-set temperature is preferably in the range of ±5° C. of a softening point of the film.

The first roll 452 comprises a plurality of first male elements. In one embodiment, the plurality of first male elements are formed as rows of circumferentially-spaced teeth 410 that extend in spaced relationship about at least a portion of roll 452. Teeth 410 can be arranged in a staggered pattern. Teeth 410 extend radially outwardly from the surface of the roll 452 to engage grooves 408 of roll 454. The engagement of the teeth 410 and the grooves 408 is shown in greater detail in the cross sectional representation of FIG. 7, discussed below. Both or either of rolls 452 and 454 can be heated by means known in the art such as by incorporating hot oil filled rolls or electrically-heated rolls. Alternatively, both or either of the rolls may be heated by surface convection or by surface radiation.

Teeth 410 can be joined to roll 452. The term "joined to" encompasses configurations in which an element is secured to another element at selected locations, as well as configurations in which an element is completely secured to another element across the entire surface of one of the elements. The term "joined to" includes any known manner in which elements can be secured including, but not limited to mechanical entanglement. Teeth can be attached to, such as by welding, compression fit, or otherwise joined. However, "joined to" also includes integral attachment, as is the case for teeth machined by removing excess material from roll 452. The location at which teeth 410 are joined to roll 452 is a base of a tooth. At any cross-sectional location parallel to the base of each tooth can have a round or a non-round cross-sectional area. In an alternate embodiment, the teeth may comprise pins that are rectangular or other shapes depending on the corresponding second element shape desired.

The second roll 454 can comprise a plurality of first female elements. In one embodiment, the plurality of first female elements are discrete grooves or voids 408 into which one or more of teeth 410 of roll 452 mesh. The groove 408 may have the same shape as a base of the teeth 410 and slightly larger dimensions on all edges and side than the base of the teeth 410. The depth of the grooves 408 may be deeper than a height of the teeth 410. The grooves 408 may or may not be tapered. In the case, the spacing of second elements is limited by the spacing of the grooves 408 on roll 454. A center-to-center distance of two adjacent teeth is a measure between centers of two adjacent teeth. A point where a major axis and a minor axis of a tooth cross each other is determined as the center of the tooth.

FIG. 7 shows in cross section a portion of the first roll 452 having first male elements such as teeth 10 and the second roll 454 intermeshing each other including representative teeth 410. As shown, teeth 410 have tooth height TH, depth of engagement E, and gap clearance C. A tooth height TH may range from about 0.5 mm to about 10 mm Depth of engagement E is a measure of the level of engaging rolls 452 and 454 and is measured from a top surface of the roll 454 to top 412 of tooth 410 of the roll 452. Gap clearance C is a distance between a top surface of the roll 454 and a bottom surface of the roll 452 when rolls 452 and 454 are in maximum engagement. Gap clearance is preferably wide enough to prevent the first elements, especially when the first elements are discrete extended elements, formed in a precursor web from heat-induced damages from second element forming step, and thus the first elements remain substantially intact during second element formation process and softness as well as fluid handling of the web is not hindered. Heat-induced damages include permanent deformation of at least part the first elements which may cause decrease in diameters of distal open ends of the first elements, hardening part of the first elements as a result of exposure to the heat. Gap clearance preventing from heat-induced damages can be determined in consideration of precursor web property, precursor web thickness, height of microtextures, second element formation process operation conditions such as roll temperature and production speed.

It is also contemplated that the size, shape, orientation and spacing of the teeth 410 can be varied about the circumference and width of roll 452 to provide for varied laminate web 1 properties and characteristics.

Additionally, substances such as lotions, ink, surfactants, and the like can be sprayed, coated, slot coated, extruded, or otherwise applied to Laminate web 1 before or after entering nip 456. Any processes known in the art for such application of treatments can be utilized.

Figure 8:
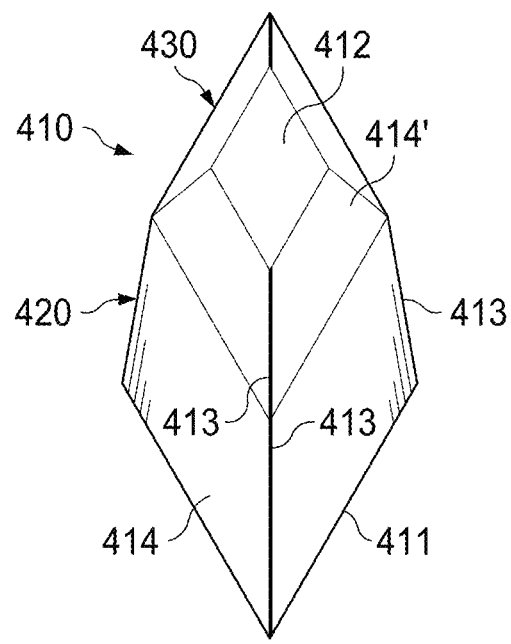
FIG. 8 is a schematic representation of an exemplary tooth for a second element forming unit for producing one embodiment of laminate webs of the present invention.
Figure 9:
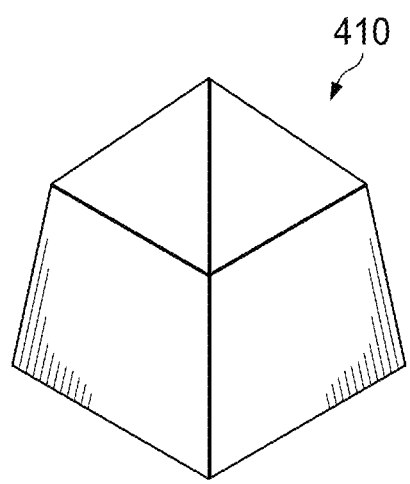
FIG. 9 is a schematic representation of another exemplary tooth for a second element forming unit forming another embodiment of laminate webs of the present invention.

Perspective views of exemplary configuration for tooth 410 are shown in FIGS. 8 and 9. As shown in FIG. 8, each tooth 410 has a base 411, a tooth top 412, edges 413 and sides 414. Edges 413 and sides 414 may be slightly rounded. Teeth 410 can have a base in a generally polygonal shape. For example, at their base 411, the cross section of teeth 410 can have a tooth cross-sectional length TL and a tooth cross-sectional width TW exhibiting a tooth aspect ratio AR of TL/TW of not greater 3.3, or not greater than 2.5, or not greater than 2, or not greater than 1.9. In one embodiment, each of the teeth has a quadrilateral shape base. The teeth 410 are tapered from the base to the top. In one embodiment, a degree of taper may not be constant along the height of the teeth shown in FIG. 8. In another embodiment, a degree of taper may be constant along the height of the teeth. The tooth 410 may comprise a proximal part 420 joined to a member of a second element forming unit, and a distal part 430 directly adjacent to the proximal part and tapering to a tooth top 412. The tooth 410 may comprise a proximal part, a distal part, and a middle part between the proximal part 420 and the distal part 430. The proximal part and the distal part may have different degree of taper from each other. In one embodiment, the distal part 430 has a higher degree of taper than the proximal part 420. In another embodiment, at least one of the proximal part 420 and the distal part 430 has a constant degree of taper. The proximal part is generally a frustum shape tapering from a polygonal-shape base to a point. As shown in FIG. 8, a proximal part 420 can have four sides 414, each side being generally (isosceles) rectangular. The vertex of two sides makes up an edge. The vertices of edges 413 can be machined to have a rounded radius of curvature. As shown in FIG. 8, a distal part 430 can have a generally rectangular shape having at least four sides 414', each side being substantially triangular and tapering from the bottom of the distal part to a tip of the tooth. The vertex of two sides of the distal part 430 makes up an edge. The vertices of edges 413' can be relatively sharp, or can be machined to have a rounded radius of curvature. The tooth top 412 can be flatten, or otherwise slightly shaped so as to stretch but not to puncture the precursor laminate web 30.

In one embodiment, a flattened tooth top 412 can transition to sides 414 and the transition can be at a radius of curvature, providing for a smooth, rounded, flattened tooth top. Without being bound by theory, it is believed that having relatively a smooth, rounded, flattened tooth top permits the teeth 410 to form second elements 7 without resulting in apertures or tearing in second elements 7, especially in base 71.

FIG. 9 is another exemplary tooth for a second element forming unit forming.

Figure 10:
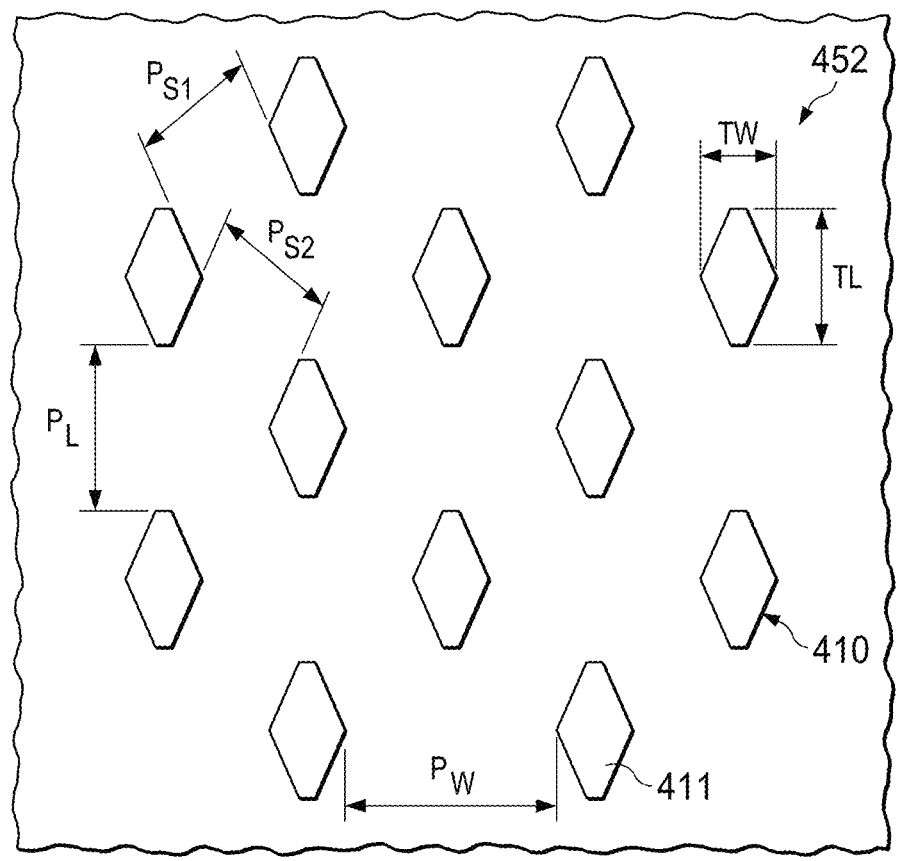
FIG. 10 is a schematic representation of a configuration of teeth in a second element forming unit for producing a laminate web of the present invention.

An exemplary configuration for teeth 410 and arrangement thereof are shown in FIG. 10. Dimensions and a shape of teeth 410 in FIG. 10 are slightly different from those of tooth 410 in FIG. 8. Teeth 410 in FIG. 10 having a cross sectional length TL and a cross sectional width TW are arranged in a staggered pattern to have a tooth-to-tooth spacing $P_L$ between two adjacent teeth along the cross-sectional length dimension, a tooth-to-tooth spacing $P_W$ between two adjacent teeth along the cross-sectional width dimension, and a tooth-to-tooth spacing $P_S$ between two adjacent teeth along a line that is not parallel either to the cross-sectional length dimension or to the cross-sectional width dimension. The teeth 410 may have different lengths of tooth-to-tooth spacing $P_{S1}$ and $P_{S2}$, depending on teeth configuration. In one embodiment as shown in FIG. 10, each of $P_{S1}$ and $P_{S2}$ is constant between two staggered adjacent teeth, i.e., between two adjacent teeth along a line that is not parallel either to the cross-sectional length dimension or to the cross-sectional width dimension, and it may be effective to minimize a flat area in the land area where fluid tends to be trapped in valleys between first elements. For such purposes, lozenge-shaped teeth are preferred especially when they are arranged in a staggered way as the shapes can provide second elements on the web 1 well nested and minimize the land area between second elements. Lozenge-shaped teeth may also strain and relax the web 1 to form slight arches in the land area between two adjacent second elements. By referring to FIG. 10, the base 411 has a hexagonal shape by slightly cutting out two opposite edges 413 of the proximal part. Edges 413' of the distal part 430 corresponding to the two opposite edges 413 of the proximal part also can be cut out.

In one embodiment, a tooth-to-tooth spacing $P_S$ between two adjacent teeth along a line that is not parallel either to the cross-sectional length dimension or to the cross-sectional width dimension not greater than or equal to about 1.5 mm. In another embodiment, at least one of the tooth-to-tooth spacing $P_L$ and $P_W$ is greater than about 1.5 mm.

Of course, tooth-to-tooth spacings $P_L$, $P_W$ and/or $P_S$, tooth cross sectional length TL, and tooth cross sectional width TW can each be varied independently.

It can be appreciated by the forgoing description that when web 1 is made by the apparatus and method of the present invention that the precursor laminate web 30 is stretched during the second element formation process on the condition that the strain that the second precursor web 21 receives is below the strain to break of the second precursor web 21 so that the second precursor web 21 elongates to the extent necessary to form second elements without failure, e.g., failure due to tensile stresses which causes ruptures or tearings in the second precursor web 21.

For a given maximum strain (e.g., the strain imposed by teeth 410 on a forming member such as a roll) to form second elements, second precursor web 21 should not fail under the tensile loading produced by the imposed strain locally (i.e., in the area of strain). Relative elongation to break values of webs used in the present invention can be measured by means known in the art, such as by standard tensile testing methods using standard tensile testing apparatuses, such as those manufactured by Instron, MTS, Thwing-Albert, and the like.

Figure 11A:
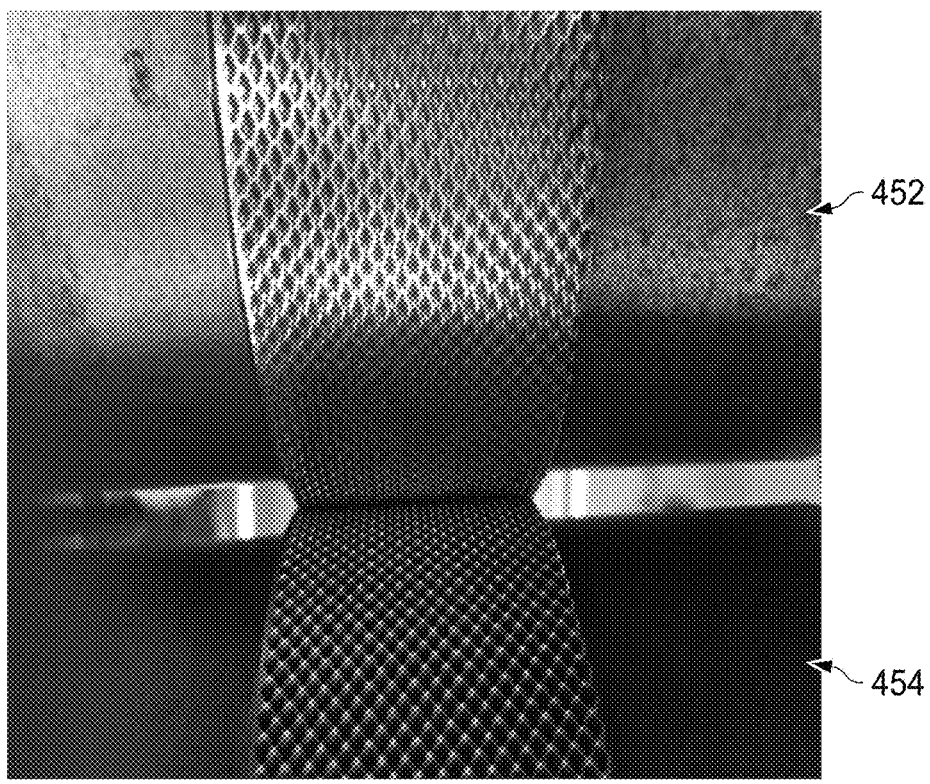
FIG. 11A is a view of intermeshing engagement of a portion of a second element forming unit for producing one embodiment of laminate webs of the present invention.
Figure 11B:
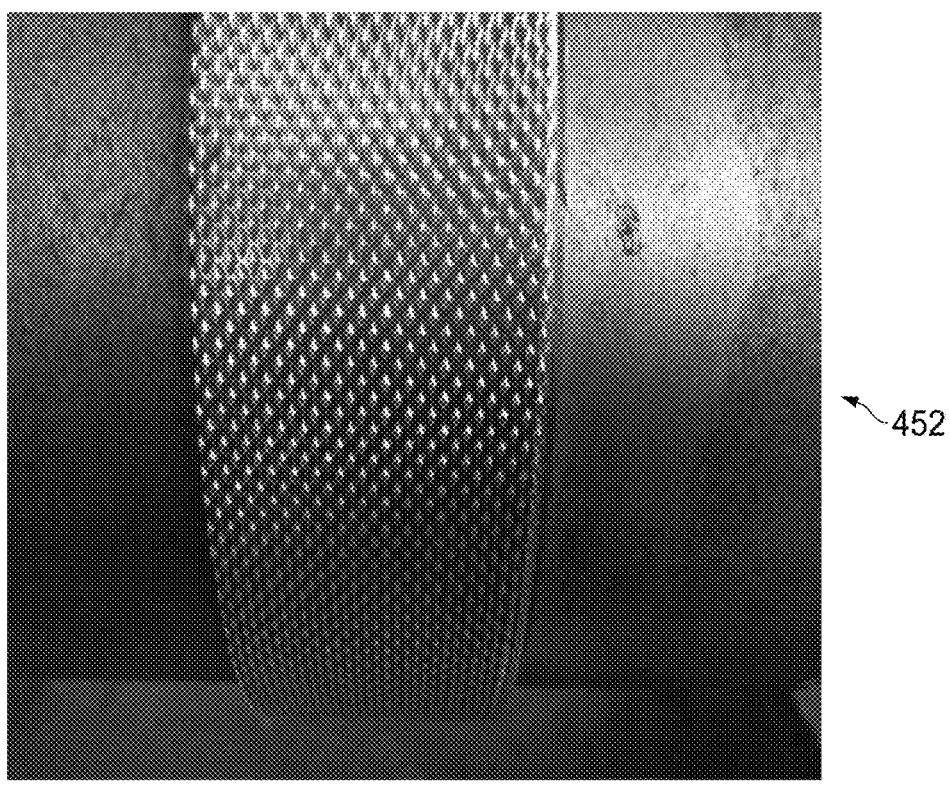
FIG. 11B is a view of a portion of a first member of a second element forming unit in FIG. 11A.
Figure 11C:
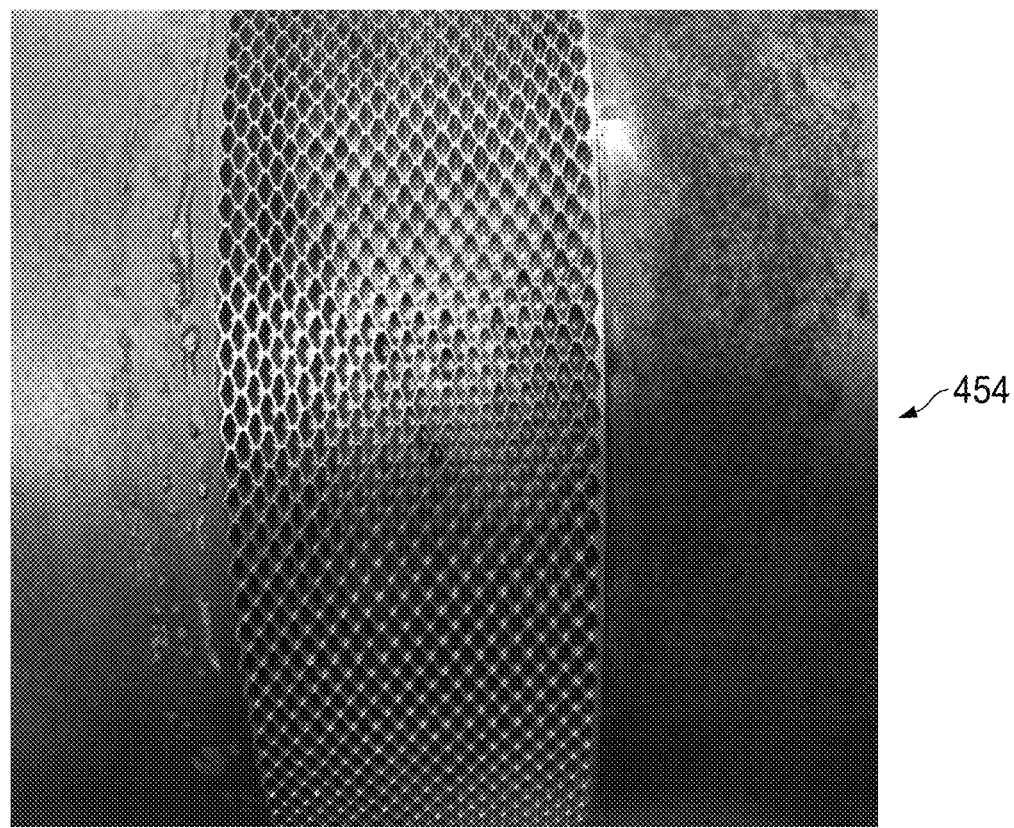
FIG. 11C is a view of a portion of a second member of a second element forming unit in FIG. 11A.
Figure 12:
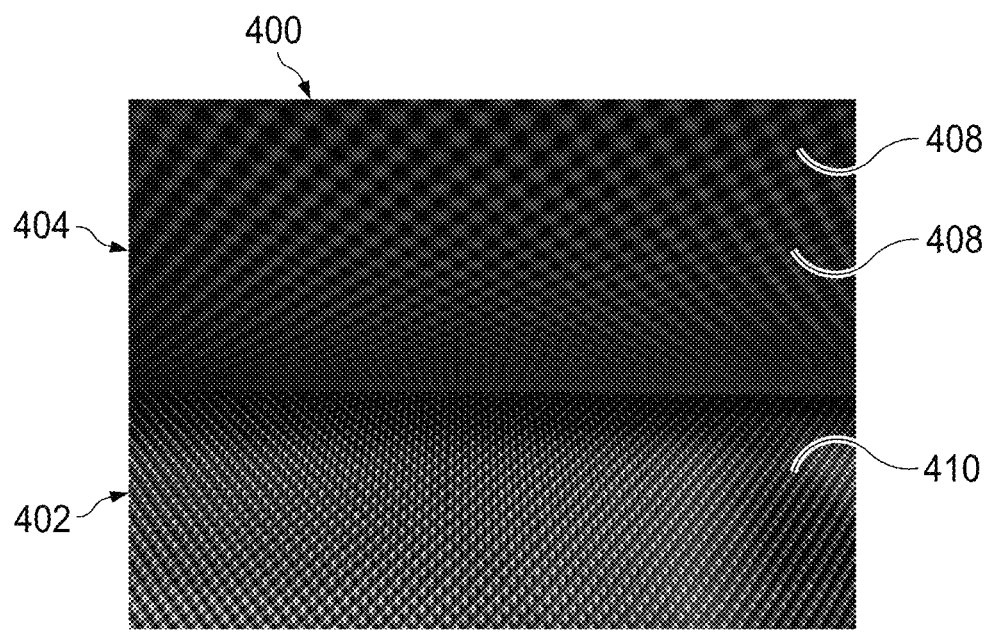
FIG. 12 is a view of intermeshing engagement of a portion of a second element forming unit forming a laminate web of another embodiment of the present invention.

FIG. 11A shows a portion of an exemplary second element forming unit having a roll 452 having teeth and a roll 454 intermeshing with roll 452. FIG. 11B shows a portion of one embodiment of a roll 452 having a plurality of teeth 410 useful for making a laminate web 1. FIG. 11C shows a portion of one embodiment of a roll 454 having a plurality of grooves 408 useful for making a laminate web 1. FIG. 12 shows a portion of another second element forming unit 400 having a roll 402 having teeth 410 and a roll 404 having grooves 408 and intermeshing with roll 452.

The number, spacing, and size of second elements 7 can be varied by changing the number, spacing, and size of teeth 410 and making corresponding dimensional changes as necessary to roll 402, 452 and/or roll 404, 454. This variation, together with the variation possible in precursor webs 20, 21 permits many varied webs 1 to be made for many purposes.

An alternative laminate web having the first elements, the second elements and third elements can be produced, for example, according to process of FIGS. 6A and 6B. Referring to FIGS. 6A and 6B, to produce such an alternative laminate web, the second roll 404 comprises a plurality of first female elements into which one or more of first male elements of the first roll 402 mesh to form the second elements, and a plurality of second male elements (not shown in the figures) to form the third elements on the precursor laminate web 30. The second male elements may be located between two first female elements. The second male elements may be surrounded by at least three first female elements. The second male elements are discrete, and may be of any suitable configuration. Descriptions of configuration of the first male elements are also applicable for the second male elements.

Application of Laminate Web

Laminate webs according to the present invention can be used in disposable absorbent articles such as bandages, wraps, incontinence devices, diapers, sanitary napkins, pantiliners, tampons, and hemorrhoid treatment pads, as well as other consumer products such as floor cleaning sheets, body wipes, and laundry sheets.

For example, the aperture web of the present invention can be used in applications such as products that contact human or non-human animal skin, such as infant-use disposable diapers, adult-use disposable diapers, sanitary napkins, panty liners, incontinence pads, interlabial pads, breast-milk pads, sweat sheets, animal-use excreta handling articles, animal-use diapers, and similar various absorbent articles; face masks, base fabric of cooling/heating pads and similar cosmetic/medical-use patches, wound surface protection sheets, nonwoven bandages, hemorrhoid pads, warming devices that directly contact the skin (e.g. disposable hand warmers), base fabric of various animal-use patches, and similar skin covering sheets; makeup removal sheets, anti-perspirant sheets, bottom wipes and similar wipes for use on a person, various wiping sheets for use on animals, and the like. The web of the present invention is preferably used as a topsheet for an absorbent article. In one embodiment, the first side of the web 1 having a plurality of discrete extended elements is in contact with the skin. In another embodiment, the second side comprising nonwoven layer of the web 1 is in contact with the skin.

Absorbent Article

An absorbent article according to the present invention comprises a topsheet and a backsheet joined to the topsheet, wherein the topsheet comprises the apertured web according to the present invention. It may further comprise an absorbent core between the topsheet and the backsheet. The absorbent articles may be produced industrially by any suitable means. The different layers may thus be assembled using standard means such as embossing, thermal bonding, or gluing or combination of both.

Topsheet

With the apertured web according to the present invention, a surface of the web having a plurality discrete extended elements is preferably, disposed on a side in contact with the skin.

Backsheet

Any conventional backsheet materials commonly used for absorbent articles may be used as backsheet. In some embodiments, the backsheet may be impervious to malodorous gases generated by absorbed bodily discharges, so that the malodors do not escape. The backsheet may or may not be breathable.

Absorbent Core

It may be desirable that the article further comprises an absorbent core disposed between the topsheet and the backsheet. As used herein, the term "absorbent core" refers to a material or combination of materials suitable for absorbing, distributing, and storing fluids such as urine, blood, menses, and other body exudates. Any conventional materials for absorbent core suitable for absorbent articles may be used as absorbent core.

Test Methods

Artificial Menstrual Fluid ("AMF") Preparation

AMF is composed of a mixture of defibrinated sheep blood, a phosphate buffered saline solution and a mucous component, and has a viscosity between 7.15 to 8.65 cSt at 23° C.

Viscosity on the AMF is performed using a low viscosity rotary viscometer such as Cannon LV-2020 Rotary Viscometer with UL adapter (Cannon Instrument Co., State College, US) or equivalent. The appropriate size spindle for the viscosity range is selected, and instrument is operated and calibrated as per the manufacturer. Measurements are taken at 23° C.±1 C.° and at 60 rpm. Results are reported to the nearest 0.01 cSt.

Defibrinated Sheep Blood

Defibrinated sheep blood with a packed cell volume of 38% or greater collected under sterile conditions (available from Cleveland Scientific, Inc., Bath, OH, US) or equivalent is used.

Phosphate Buffered Saline Solution

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. Add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

Mucous Component

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. A successful range of gastric mucin is usually between 38 to 50 grams. To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5C°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range, then remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1C°.

Allow the temperature of the sheep blood and mucous component to come to 23° C.±1 C°. Using a 500 mL graduated cylinder, measure the volume of the entire batch of the mucous component and add it to a 1200 mL beaker. Add an equal volume of sheep blood to the beaker and mix thoroughly. Using the viscosity method previously described, ensure the viscosity of the AMF is between 7.15-8.65 cSt. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 C°. Any unused portion is discarded after testing is complete.

Acquisition Time Measurement

Acquisition time is measured for an absorbent article loaded with Artificial Menstrual Fluid (AMF) as described herein, using a strikethrough plate and an electronic circuit interval timer. The time required for the absorbent article to acquire a dose of AMF is recorded. All measurements are performed in a laboratory maintained at 23° C.±2 C.° and 50%±2% relative humidity.

Referring to FIGS. 21A-21E, the strikethrough plate 9001 is constructed of Plexiglas with an overall dimension of 10.2 cm long by 10.2 cm wide by 3.2 cm tall. A longitudinal channel 9007 running the length of the plate is 13 mm deep and 28 mm wide at the top plane of the plate, with lateral walls that slope downward at 65° to a 15 mm wide base. A central test fluid well 9009 is 26 mm long, 24 mm deep and 38 mm wide at the top plane of the plate with lateral walls that slope downward at 65° to a 15 mm wide base. At the base of the test fluid well 9009, there is an "H" shaped test fluid reservoir 9003 open to the bottom of the plate for the fluid to be introduced onto the underlying article. The test fluid reservoir 9003 has an overall length ("L") of 25 mm, width ("W") of 15 mm, and depth ("D") of 8 mm. The longitudinal legs of the reservoir are 4 mm wide and have rounded ends with a radius 9010 of 2 mm. The legs are 3.5 mm apart.

The central strut has a radius 9011 of 3 mm and houses the opposing electrodes 9004 6 mm apart. The lateral sides of the reservoir bow outward at a radius 9012 of 14 mm bounded by the overall width, W, of 15 mm Two wells 9002 (80.5 mm long×24.5 mm wide×25 mm deep) located outboard of the lateral channel, are filled with lead shot to adjust the overall mass of the plate to provide a constraining pressure of 0.25 psi (17.6 gf/cm²) to the test area. Electrodes 9004 are embedded in the plate 9001, connecting the exterior banana jacks 9006 to the inside wall of the fluid reservoir 9003. A circuit interval timer is plugged into the jacks 9006 to the inside wall 9005 of the fluid reservoir 9003. A circuit interval timer (not shown in the drawings) is plugged into the jacks 9006, and monitors the impedance between the two electrodes 9004, and measures the time from introduction of the AMF into reservoir 9003 until the AMF drains from the reservoir. The timer has a resolution of 0.01 sec.

Test products are removed from all packaging using care not to press down or pull on the products while handling. No attempt is made to smooth out wrinkles. The test samples are conditioned at 23° C.±2 C.° and 50%±2% relative humidity for at least 2 hours prior to testing.

The required mass of the strikethrough plate must be calculated for the specific dimensions of the test article such that a confining pressure of 1.72 kPa is applied. Determine the longitudinal and lateral midpoint of the article's absorbent core. Measure and record the lateral width of the core to the nearest 0.1 cm. The required mass of the strikethrough plate is calculated as the core width multiplied by strikethrough plate length (10.2 cm) multiplied by 17.6 gf/cm² and recorded to the nearest 0.1 g. Add lead shot to the plate to achieve the calculated mass.

Connect the electronic circuit interval timer to the strikethrough plate 9001 and zero the timer. Place the test product onto a flat, horizontal surface with the body side facing up. Gently place the strikethrough plate 9001 onto the center of the test product ensuring that the "H" shaped reservoir 9003 is centered over the test area.

Using a mechanical pipette, accurately pipette 4.00 mL±0.05 mL of AMF into the test fluid reservoir 9003. The fluid is dispensed, without splashing, along the molded lip of the bottom of the reservoir 9003 within a period of 3 seconds or less. After the fluid has been acquired, record the acquisition time to the nearest 0.01 second. Thoroughly clean the electrodes 9004 before each test.

In like fashion, a total of three (3) replicate samples are tested for each test product to be evaluated. Report the Acquisition Time (sec) as the mean of the replicates to the nearest 0.01 sec.

Stain Perception Measurement

Stain perception is measured by the size and color intensity of a fluid stain visible on an absorbent article. Artificial menstrual fluid (AMF) is dosed onto the surface of an article, and is photographed under controlled conditions. The photographic image is then calibrated and analyzed using image analysis software to obtain measurements of the size and color intensity of the resulting visible stain. All measurements are performed at constant temperature (23° C.±2) C.° and relative humidity (50%±2%).

The absorbent article, a calibrated color standard containing 24 standard color chips such as ColorChecker Passport (X-Rite; Grand Rapids, MI, US) or equivalent, and a calibrated ruler are laid horizontally flat on a matte black background inside a light box that provides stable uniform lighting evenly across the entire base of the light box. A suitable light box is the Sanoto MK50 (Sanoto, Guangdong, China), or equivalent, which provide an illumination of 5500 LUX at a color temperature of 5500K. A Digital Single-Lens Reflex (DSLR) camera with manual setting controls (e.g. a Nikon D40x available from Nikon Inc., Tokyo, Japan, or equivalent) is mounted directly above an opening in the top of the light box so that the entire article, color standard and ruler are visible within the camera's field of view.

Using a standard 18% gray card (e.g., Munsell 18% Reflectance (Gray) Neutral Patch/Kodak Gray Card R-27, available from X-Rite; Grand Rapids, MI, US or equivalent), the camera's white balance is custom set for the lighting conditions inside the light box. The camera's manual settings are set so that the image is properly exposed such that there is no signal clipping in any of the color channels. Suitable settings might be an aperture setting of f/11, an ISO setting of 400, and a shutter speed setting of 1/400 sec. At a focal length of 35 mm the camera is mounted approximately 14 inches above the article. The image is properly focused, captured, and saved as a JPEG file. The resulting image must contain the entire article, color target, and calibrated ruler at a minimum resolution of 15 pixels/mm.

Absorbent article samples are conditioned at 23° C.±2 C.° and 50%±2% relative humidity for 2 hours prior to testing. Place a sample article flat, with the top sheet of the sample facing upward, on the matte surface within the light box along with the ruler and color standard. Using a mechanical pipette held approximately 5 mm above the sample surface, a loading of 1.0 mL±0.05 mL of AMF is slowly and steadily loaded onto the center of the article over a 5 second time period. Two additional 1.0 mL loadings are applied in the same location and in like fashion at 2 minute intervals for a total of 3.0 mL of AMF. Images are captured at 2 minutes and again at 5 minutes after the third loading.

To analyze the image, it is first transferred to a computer running an image analysis software (a suitable software is MATLAB, available from The Mathworks, Inc, Natick, MA, or equivalent).

The image is color calibrated using the true tristimulus XYZ color space values provided by the manufacturer for each of the 24 color chips in the color target. If target values are given in L*a*b* they are converted to XYZ according to the standard equations. The values are identified as $X_{true1 \ldots 24}$, $Y_{true1 \ldots 24}$, and $Z_{true1 \ldots 24}$. Using the image analysis software the mean red, green, and blue (RGB) values of each of the 24 color chips in the image are measured using a square region of interest that covers approximately 75% of the interior area of each individual color chips. These values are identified as $R_{1 \ldots 24}$, $G_{1 \ldots 24}$, and $B_{1 \ldots 24}$. A system of 24 equations, using the $X_{true}$ and associated RGB values for each color tile, is set up according to the following example:

$$X_{true1} = \alpha_1 + \alpha_2 R_1 + \alpha_3 G_1 + \alpha_4 B_1 + \alpha_5 R_1^2 + \alpha_6 R_1 G_1 + \alpha_7 G_1^2 + \alpha_8 R_1 B_1 + \alpha_9 G_1 B_1 + \alpha_{10} B_1^2$$

$$X_{true24} = \alpha_1 + \alpha_2 R_{24} + \alpha_3 G_{24} + \alpha_4 B_{24} + \alpha_5 R_{24}^2 + \alpha_6 R_{24} G_{24} + \alpha_7 G_{24}^2 + \alpha_8 R_{24} B_{24} + \alpha_9 G_{24} B_{24} + \alpha_{10} B_{24}^1$$

A second system of 24 equations, using the $Y_{true}$ and associated RGB values for each color tile, is set up according to the following example:

$$Y_{true1} = \beta_1 + \beta_2 R_1 + \beta_3 G_1 + \beta_4 B_1 + \beta_5 R_1^2 + \beta_6 R_1 G_1 + \beta_7 G_1^2 + \beta_8 R_1 B_1 + \beta_9 G_1 B_1 + \beta_{10} B_1^2$$

$$Y_{true24} = \beta_1 + \beta_2 R_{24} + \beta_3 G_{24} + \beta_4 B_{24} + \beta_5 R_{24}^2 + \beta_6 R_{24} G_{24} + \beta_7 G_{24}^2 + \beta_8 R_{24} B_{24} + \beta_9 G_{24} B_{24} + \beta_{10} B_{24}^1$$

A third system of 24 equations, using the $Z_{true}$ and associated RGB values for each color tile, is set up according to the following example:

$$Z_{true1} = \gamma_1 + \gamma_2 R_1 + \gamma_3 G_1 + \gamma_4 B_1 + \gamma_5 R_1^2 + \gamma_6 R_1 G_1 + \gamma_7 G_1^2 + \gamma_8 R_1 B_1 + \gamma_9 G_1 B_1 + \gamma_{10} B_1^2$$

$$Z_{true24} = \gamma_1 + \gamma_2 R_{24} + \gamma_3 G_{24} + \gamma_4 B_{24} + \gamma_5 R_{24}^2 + \gamma_6 R_{24} G_{24} + \gamma_7 G_{24}^2 + \gamma_8 R_{24} B_{24} + \gamma_9 G_{24} B_{24} + \gamma_{10} B_{24}^1$$

Using the 24 $X_{true}$ equations, each of the ten α coefficients are solved for using the standard equation y=Ax, where y are the $X_{true}$, $Y_{true}$, and $Z_{true}$ vectors, A is the list of the measured RGB intensities, and x is a vector of the unknown alpha (α), beta (β), or gamma (γ) coefficients to be estimated.

For example, to solve for the α's in the transform that converts the RGB colors into colorimetric X tristimulus value, the arrays are as follows:

$$\hat{x} = \begin{bmatrix} \alpha_1 \\ \vdots \\ \alpha_{10} \end{bmatrix}$$

$$A = \begin{bmatrix} 1 & R_1 & G_1 & B_1 & R_1^2 & \ldots & B_1^2 \\ \vdots & \vdots & \vdots & \vdots & \vdots & \ddots & \vdots \\ 1 & R_{24} & G_{24} & B_{24} & R_{24}^2 & \ldots & B_{24}^2 \end{bmatrix}$$

$$y = \begin{bmatrix} X_{true1} \\ \vdots \\ X_{true24} \end{bmatrix}$$

The solution of the normal equations for x provides the least squares solution for the ten α coefficients according to the following equation:

$$\hat{x} = (A^T A)^{-1} A^T y$$

This procedure is repeated using the 24 $Y_{true}$ equations to solve for the ten β coefficients, and the 24 $Z_{true}$ equations to solve for the ten γ coefficients.

These coefficients are then plugged back into the original equations to provide three transform equations one each for X, Y, and Z, by which the RGB values for each individual pixel in the image are transformed into calibrated XYZ values. For example, the RGB transform equation for X using the 10 α coefficients is as follows:

$$X = \alpha_1 + \alpha_2 R + \alpha_3 G + \alpha_4 B + \alpha_5 R^2 + \alpha_6 RG + \alpha_7 G^2 + \alpha_8 RB + \alpha_9 GB + \alpha_{10} B^2$$

The XYZ values are then converted into CIE 1976 L*a*b* values as defined in CIE 15:2004 section 8.2.1.1 using D65 reference white.

The image resolution is calibrated using the calibrated distance scale in the image to determine the number of pixels per millimeter. Separate images are generated for each of the individual L*, a*, and b* channels. The Chroma image is calculated using the following formula:

$$\text{Chroma} = \sqrt{(a^*)^2 + (b^*)^2}$$

Where a* and b* are the individual colorimetric images. The chroma image is analyzed by manually drawing the region of interest (ROI) boundary around the visibly discernable perimeter of the stain. The area of the ROI is calculated and recorded to the nearest 0.1 mm$^2$ and the mean Chroma value within the ROI is calculated and recorded to the nearest 0.1 units.

The same ROI is analyzed for the a* image alone, and the mean a* value within the ROI is calculated and recorded to the nearest 0.1 units.

A minimum bounding rectangle is drawn around the ROI. This is the smallest rectangle that can be drawn within which all of the points of the ROI lie. The edges of the rectangle are parallel and perpendicular to the longitudinal and lateral axis of the absorbent article, such that the ROI height (H) is defined as the height of the bounding rectangle along the longitudinal axis of the article, and the ROI width (W) is defined as the width of the bounding rectangle along the lateral axis of the article. Both H and W are recorded to the nearest 0.1 mm.

This entire procedure is repeated on three substantially similar replicate articles. The reported value is the average of the three individual recorded measurements for stain area to the nearest 0.1 mm², mean Chroma and a* to the nearest 0.1 units, and H and W to the nearest 0.1 mm. All measurements are made and recorded separately for both the photographic images collected at the 2 minute and 5 minute time points.

Fiber-Fiber Distance Measurement

Z-direction distances between individual fibers in a nonwoven layer in a laminate sample having a film layer and a nonwoven layer is measured using micro-CT fiber-to-fiber distance measurement based on analysis of a 3D x-ray image of a sample obtained on a micro-CT instrument having a cone beam microtomograph with a shielded cabinet such as Scanco μCT 50 (Scanco Medical AG, Switzerland) and equivalents. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. Multiple individual projection images of the sample, generated as it is rotated, are collected and then reconstructed into a single 3D image. The instrument is interfaced with a computer running software to control the image acquisition and reconstruction of the raw data into a 3D image. The 3D image is then analyzed using image analysis software such as MATLAB (The Mathworks, Inc., MA, USA) and Avizo Lite (Visualization Sciences Group/FEI Company, MA, USA) and equivalents to identify and segment out the film layer from the nonwoven layer, and measure Z-direction distances between individual fibers in the nonwoven portion of the laminate sample.

Sample Preparation

To obtain a sample for measurement, lay a film-nonwoven laminate out flat and die cut a circular piece with a diameter of 7 mm. If the laminate is a component of an absorbent article, tape the absorbent article to a rigid flat surface in a planar configuration, and carefully separate the laminate from the other components of the absorbent article. A scalpel and/or cryogenic spray such as Cyto-Freeze (Control Company, TX, USA) can be used to remove the laminate from the other components of the absorbent article, if necessary, to avoid extension of the laminate. Once the laminate has been removed from the article, proceed with die cutting the sample as described above.

A sample may be cut from any location containing the laminate to be analyzed. When selecting a location for sampling, care should be taken to avoid embossed regions, if any, in the absorbent article where the laminate may have been crushed and/or compressed during the article making process, as well as any folds, wrinkles or tears.

Image Acquisition:

The micro-CT instrument is set up and calibrated according to the manufacturer's specifications. The sample is placed into an appropriate holder, between two rings of a low density material, such as foam, which have an inner diameter of at least 4 mm. This allows the central region of the sample to lay horizontal and be scanned without having any other materials directly adjacent to its upper and lower surfaces. Analysis is performed within this central region. A single 3D dataset of contiguous 3 μm isotropic voxels is collected. The 3D dataset is centered on the central analysis region, having dimensions of 7 mm on each side in the XY-plane and a sufficient number of slices to fully include the Z-direction of the sample. Images are acquired with the source at 45 kVp and 88 pA with no additional low energy filter. Current and voltage settings may be optimized to produce the maximum contrast in the projection data with sufficient x-ray penetration through the sample, but once optimized held constant for all substantially similar samples. A total of 3200 projection images are obtained with an integration time of 1000 ms and 3 averages. The projection images are reconstructed using acquisition and reconstruction software accompanies the instrument into a 3D dataset having an isotropic spatial resolution of 3 μm, and saved in 16-bit RAW format to preserve the full detector output signal for analysis.

Image Processing:

The 3D dataset is loaded into the image analysis software, and trimmed to a rectangular prism 3D image of the analysis region by removing the surrounding holder and the low density mounting material from the 3D dataset Trimming is performed such that the maximum amount of the sample in the analysis region is retained in the 3D image, and the empty space above and below the sample is minimized. The trimmed 3D image is scaled from 16-bit to 8-bit for the purpose of convenience in data analysis, and thresholded using Otsu's method which calculates the threshold level that minimizes the weighted intra-class variance, to separate and remove the background signal due to air, but maintain the signal from the film and fibers within the sample image. Film and/or fiber containing voxels are referred to as "material" voxels.

A connected components algorithm is executed on the trimmed 3D image, which identifies and groups together any material voxels that are 26-connected (touching one of their faces, edges, or corners) to any neighboring material voxels. Any material voxel clusters containing fewer than 1000 connected voxels are identified as noise and removed from the 3D image.

The 3D image is oriented so that the film upper surface is as close to parallel with the XY-plane as possible.

The film layer is identified and distinguished from nonwoven fibers using a Z-direction vector, such that given an XY-plane position, a typical Z-direction vector traveling from the top of the 3D image to the bottom will first pass through the film, and then pass through underlying nonwoven fibers. However, in the regions where apertures formed in the film layer, a fiber may be the first material encountered, and must be distinguished from the film layer. As an individual Z-direction vector travels from the top of the 3D image downward, there may be a series of contiguous material voxels in the vector as it passes through the first material encountered. The last material voxel in this series of contiguous material voxels is identified as a potential lower film surface or "bottom of film" voxel. This process is repeated as a Z-direction vector is passed through every XY-plane position in the 3D image, and all of the potential bottom of film voxels are identified. A connected components algorithm is once again executed on only the identified potential bottom of film voxels in the 3D image, which groups together potential bottom film voxels that are 26-connected (touching one of their faces, edges, or corners) to neighboring potential bottom of film voxels. The lower surface of the film is identified as the single largest continuous cluster of potential bottom of film voxels.

The fiber-to-fiber distance is measured along the Z-direction vectors, below the identified lower surface of the film layer from where one fiber ends to the beginning of the next underlying fiber. If no film voxel was identified in the Z-direction vector, due to a hole or aperture in the film layer, any distance measurements from that vector are ignored.

Any Z-direction vectors which do not encounter any fibers are also ignored. The median fiber-to-fiber distance of all the distance measurements in the 3D image is calculated and recorded to the nearest 0.1 µm. A total of three substantially similar replicate film-nonwoven laminate samples are analyzed in like manner, and the average of the three recorded median fiber-to-fiber distances is reported to the nearest 0.1 µm.

EXAMPLES

Example 1: Sample Preparation I

Laminate 1 having a plurality of first elements 4 and a plurality of protrusion 7P was produced according to process of FIG. 6A against second element forming unit of FIGS. 7 and 11A. 15 gsm air-through carded nonwoven produced from 6 denier PE/PET bicomponent polymers, and 12 gsm polymer film produced from polyethylene resin using a film extruder were used to produce laminate 1. The nonwoven was supplied onto the second surface of the polymer film to form a precursor laminate while the film was still softened enough to bond to the nonwoven. The precursor laminate was fed into the vacuum forming section to form first elements on the polymer film. The precursor laminate having first elements was fed to a second element forming unit to form protrusions to obtain laminate 1. The teeth are arranged in a staggered pattern, and oriented to having a major axis in a MD and a minor axis in a CD. The male roll was heated about 80° C., the softening point of the polyethylene film of the film layer.

Figure 13A:
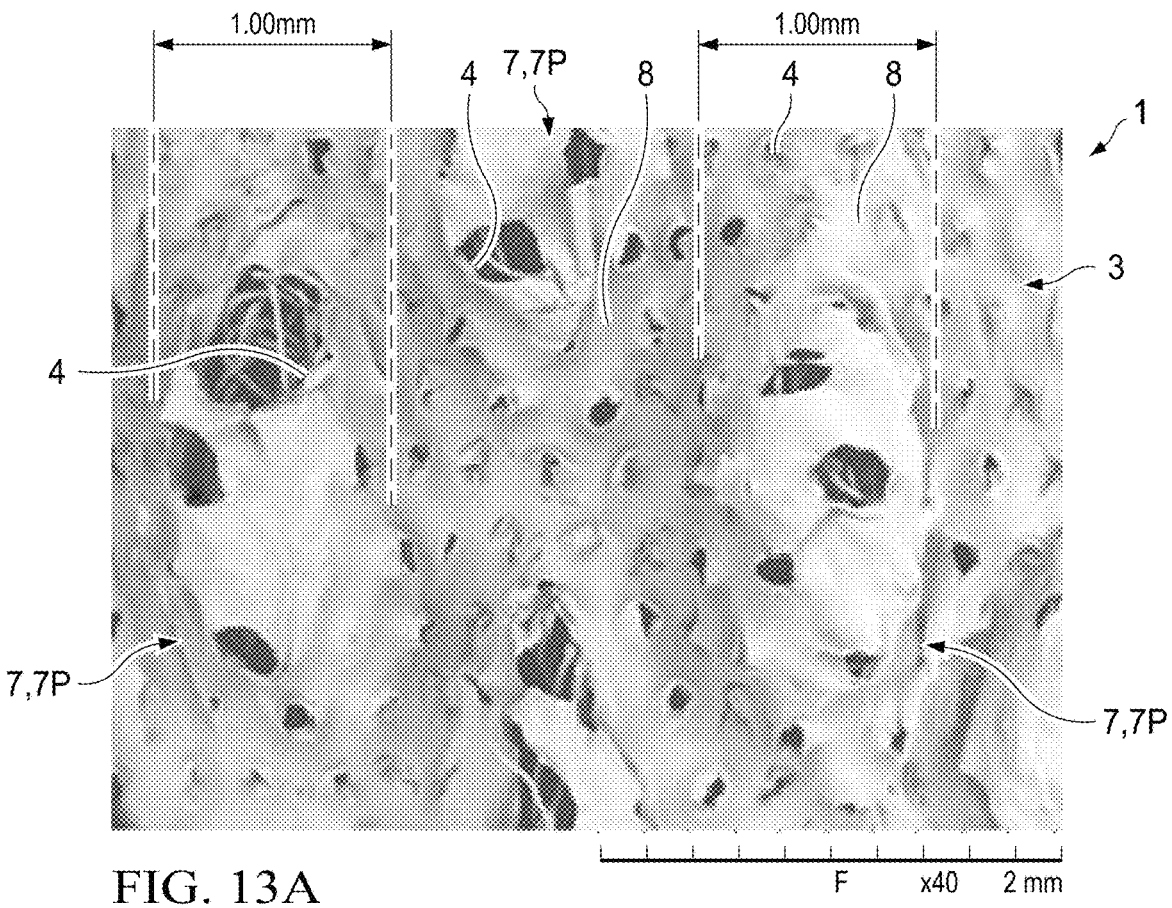
FIG. 13A is a plan view of a film side scanning electron microscope image of a laminate web having protrusions according to the present invention.
Figure 13B:
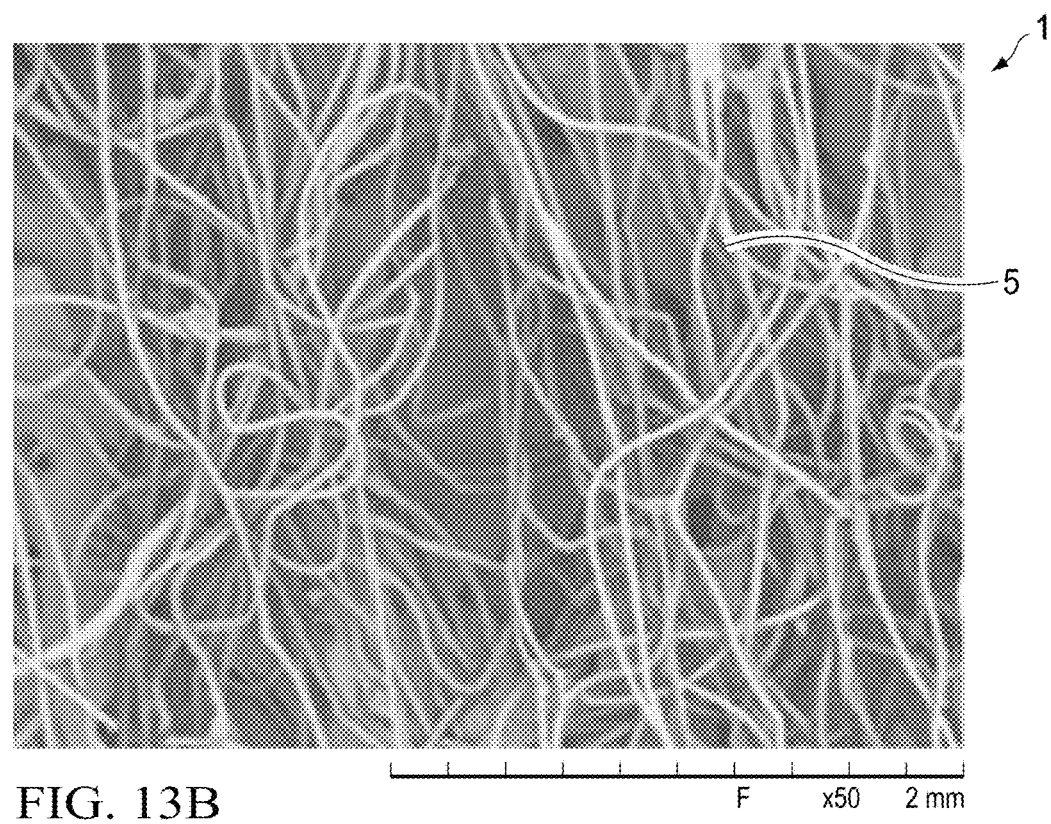
FIG. 13B is a plan view of a nonwoven side scanning electron microscope image of the laminate web of FIG. 13A.
Figure 14A:
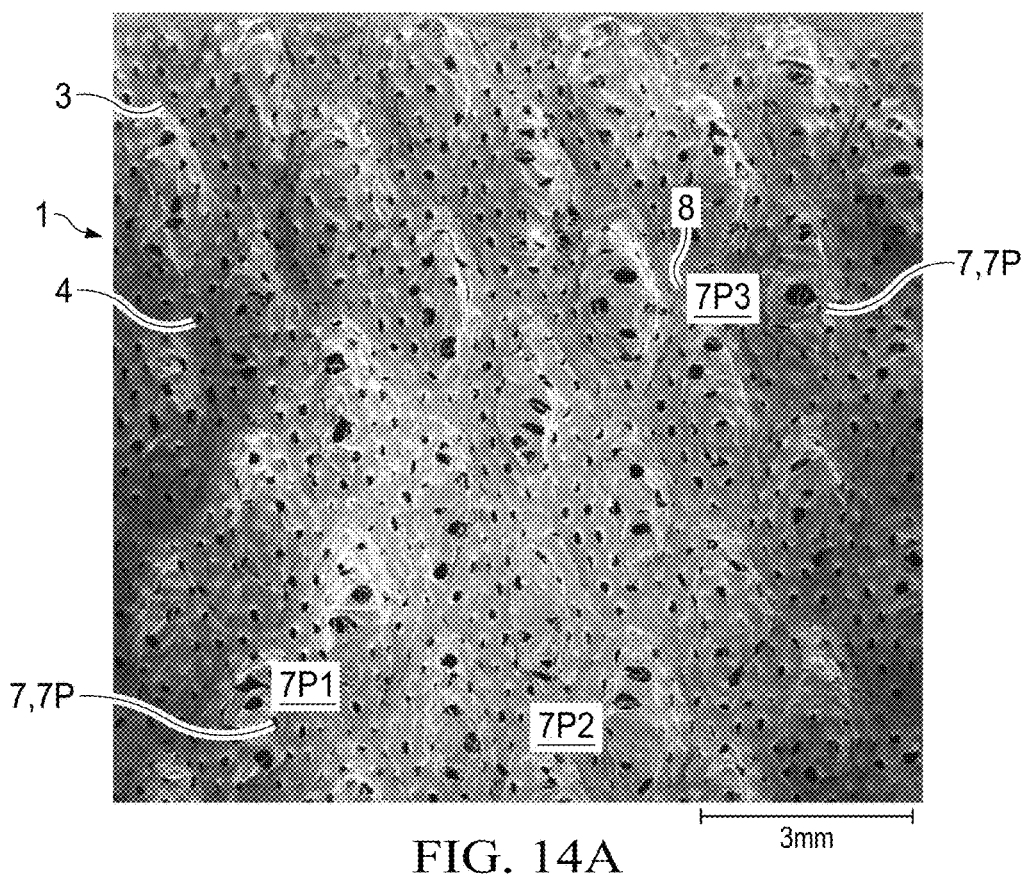
FIG. 14A is a plan view of a film side scanning electron microscope image of a laminate web having protrusions according to the present invention.
Figure 14B:
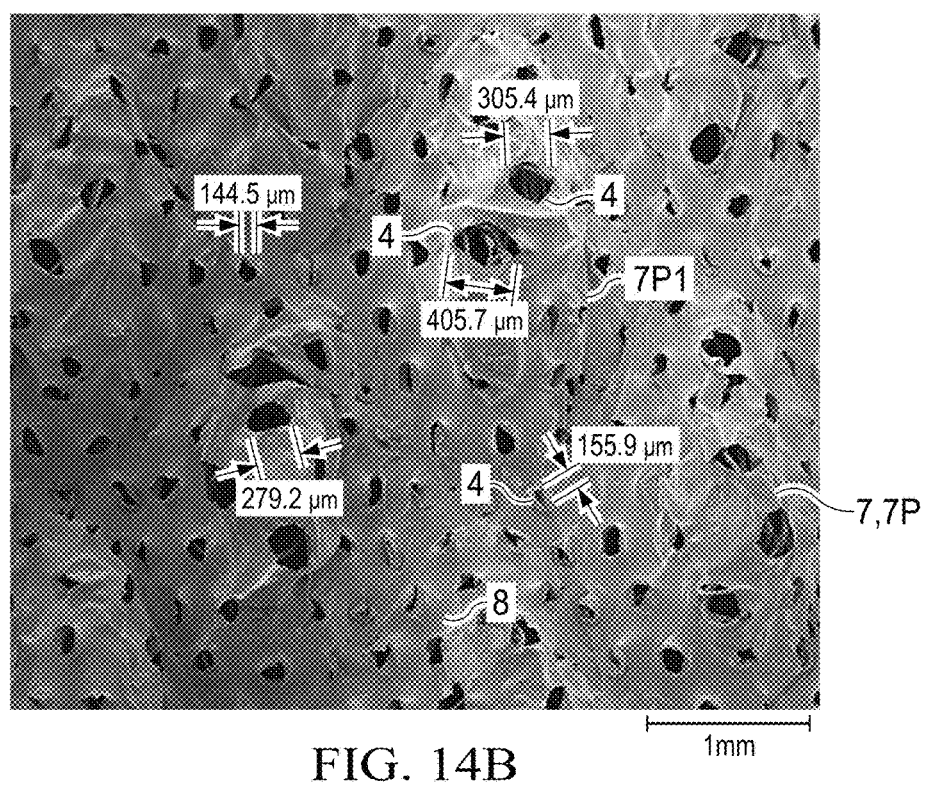
FIGS. 14B-14D are plan views of higher magnitude scanning electron microscope images of the laminate web of FIG. 14A.
Figure 14C:
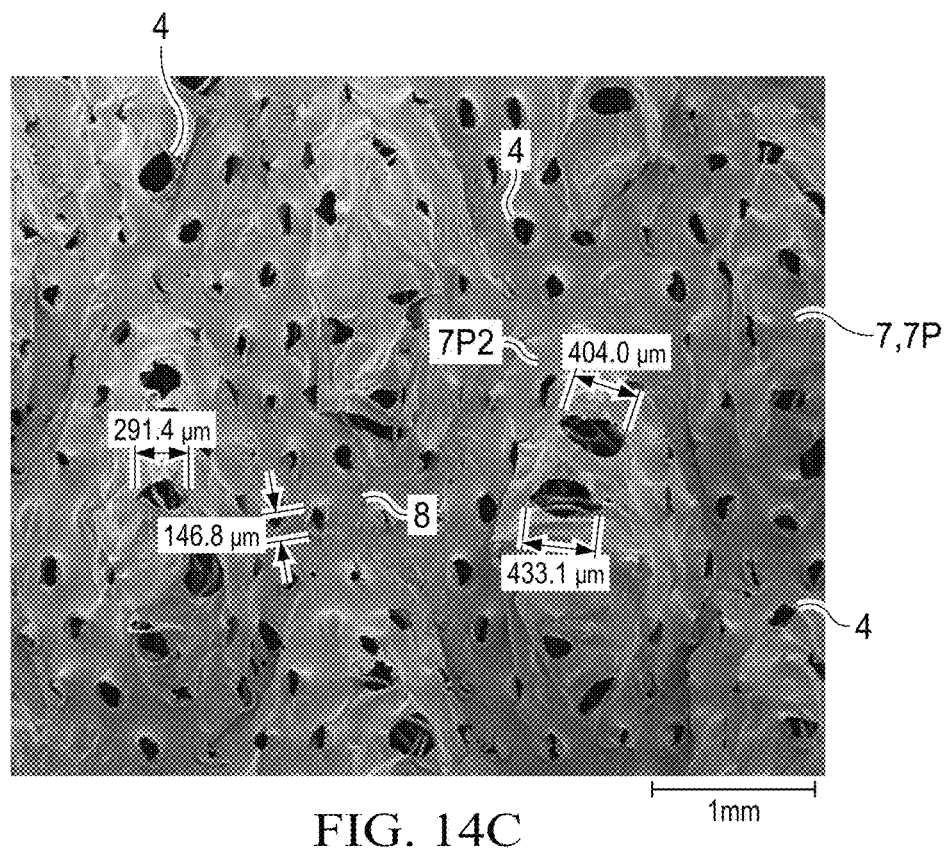
Figure 14D:
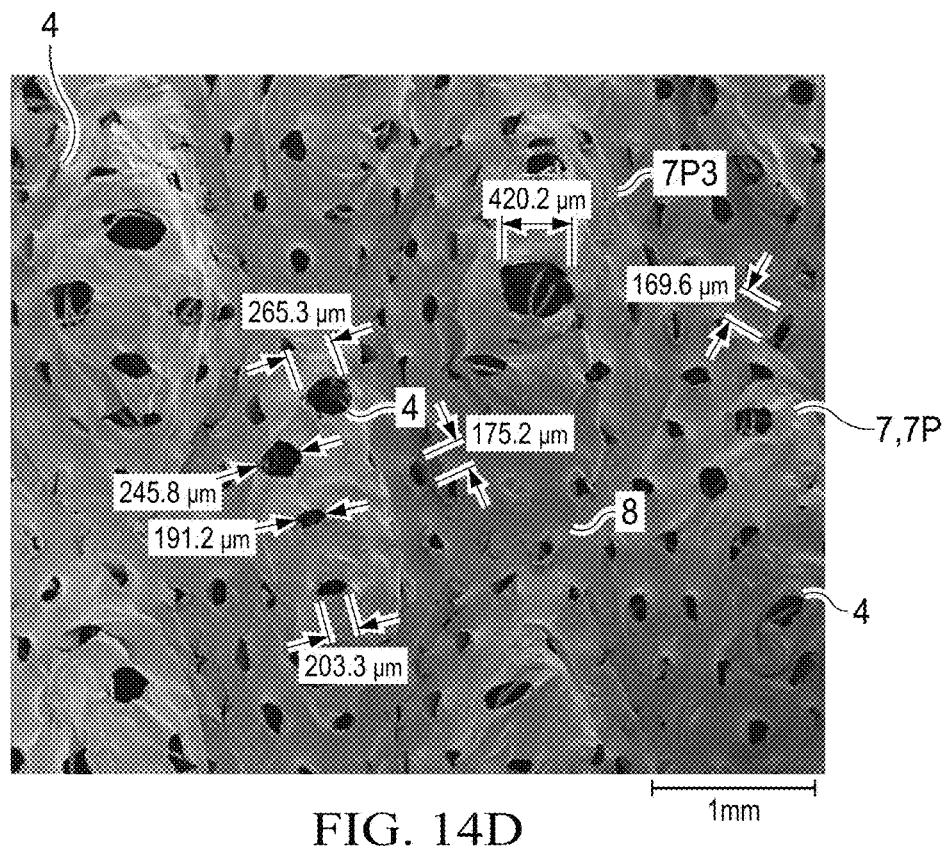

FIGS. 13A and 14A are scanning electron microscope ("SEM") (Quanta 450, FEI) images of a film side of laminate 1. FIG. 13B is a SEM (Quanta 450, FEI) image of a nonwoven side of laminate 1. 7P1, 7P2 and 7P3 in FIG. 14A indicate individual protrusions 7P. FIGS. 14B-14D are SEM (Quanta 450, FEI) images of more highly magnified portions of laminate 1 of FIG. 14A showing areas in a film side around protrusions 7P1, 7P2 and 7P3, respectively. It was observed that second elements 7, protrusions 7P in this case, have an arched wall, and a first element 4 having an enlarged open end. It was also observed that there are two adjacent protrusions 7P each of which has one or more than one first element 4 having an open distal end at least 1.5 times larger than the largest distal open end of a first element 4 in a land 8 between the two adjacent protrusions 7P. It was also observed that there is no tearings or ruptures in the protrusion 7P.

Laminate 2 having a plurality of first elements 4 and a plurality of protrusions was produced according to the same process to produce laminate 1. 15 gsm air-through carded nonwoven produced from 3 denier PE/PET bicomponent polymers, and 12 gsm polymer film produced from polyethylene resin using a film extruder were used to produce laminate 2.

Laminate 3 having a plurality of first elements 4 and a plurality of protrusions 7P was produced according to the same method employed to produce laminate 1. 10 gsm spunbond nonwoven produced from 2.5 denier PP polymers, and 12 gsm polymer film produced from polyethylene resin using a film extruder were used to produce laminate 3.

Laminates 4-6 having first elements 4 identical to those of laminate 1 and not having protrusions were produced according to the same process for producing laminate 1 except conducting the second element formation step. Laminate 4 was produced using a film layer and a nonwoven layer the same as those for laminate 1. Laminate 5 was produced using a film layer and a nonwoven layer the same as those for laminate 2, and laminate 5 was produced using a film layer and a nonwoven layer the same as those for laminate 3.

Sanitary napkin samples 1-6 were produced using Always Thin Long Super with Wing (Procter and Gamble Company, US) by removing topsheets and using laminates 1-6 produced above as topsheets, respectively. Sanitary napkins (Always Thin Long Super with Wing) were removed from packages, and unfolded. A freeze spray was applied on the topsheet side of the sanitary napkins, and topsheets were carefully removed from the sanitary napkins. Then new topsheets formed by laminates 1-6, respectively, were applied onto the topsheet-removed sanitary napkins and the new topsheet and the topsheet-removed sanitary napkins were sandwiched with no glue to obtain samples 1-6 having laminates 1-6, respectively. Samples were allowed to equilibrate to the controlled room temperature for at least two hours prior to testing.

Example 2: Sample Preparation II

Laminate 7 having a plurality of first elements 4 and a plurality of recesses 7R was produced according to the same process to produce laminate 1. 15 gsm air-through carded nonwoven produced from 6 denier PE/PET bicomponent polymers, and 12 gsm polymer film produced from polyethylene resin using a film extruder were used to produce laminate 7. The nonwoven was supplied onto the second surface of the polymer film to form a precursor laminate while the film was still softened enough to bond to the nonwoven. The precursor laminate was fed into the vacuum forming section to form first elements on the polymer film. The precursor laminate having first elements was fed to a second element forming unit to form recesses to obtain a laminate web. The teeth are arranged in a staggered pattern, and oriented to having a major axis in a MD and a minor axis in a CD. The male roller was heated about 80° C., the softening point of the polyethylene film of the film layer.

Laminate 8 having a plurality of first elements 4, a plurality of recesses 7R was produced according to the same process to produce laminate 1. 10 gsm spunbond nonwoven produced from 2.5 denier PP polymers, and 12 gsm polymer film produced from polyethylene resin using a film extruder were used to produce laminate 8.

Figure 15B:
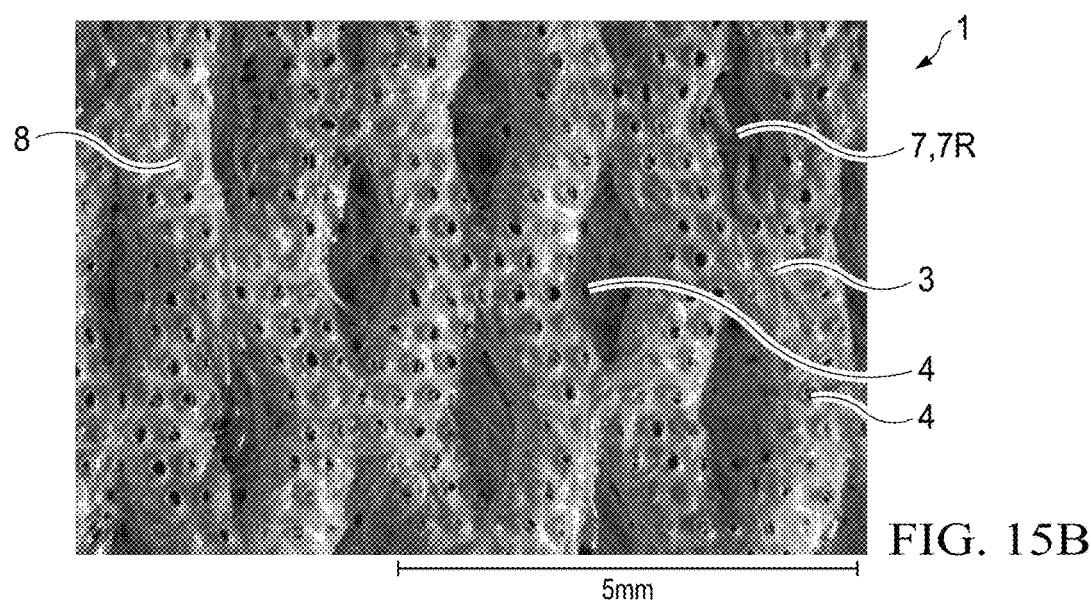
FIG. 15B is a plan view of a film side scanning electron microscope image of the laminate web of FIG. 15A.

FIGS. 15A and 15B are SEM (Quanta 450, FEI) images of a nonwoven layer side and a film side of highly magnified portions of Laminate 4, respectively. FIG. 16 is a SEM (Quanta 450, FEI) image of a cross section of laminate 7 in the width direction of the recesses 7R of laminate 7. It was observed that the recess 7R has a sloped sidewall 6 and a bottom area 10 concaved and the bottom area 10 has a very small area of plateau, and has multiple first elements having open ends.

Figure 17A:
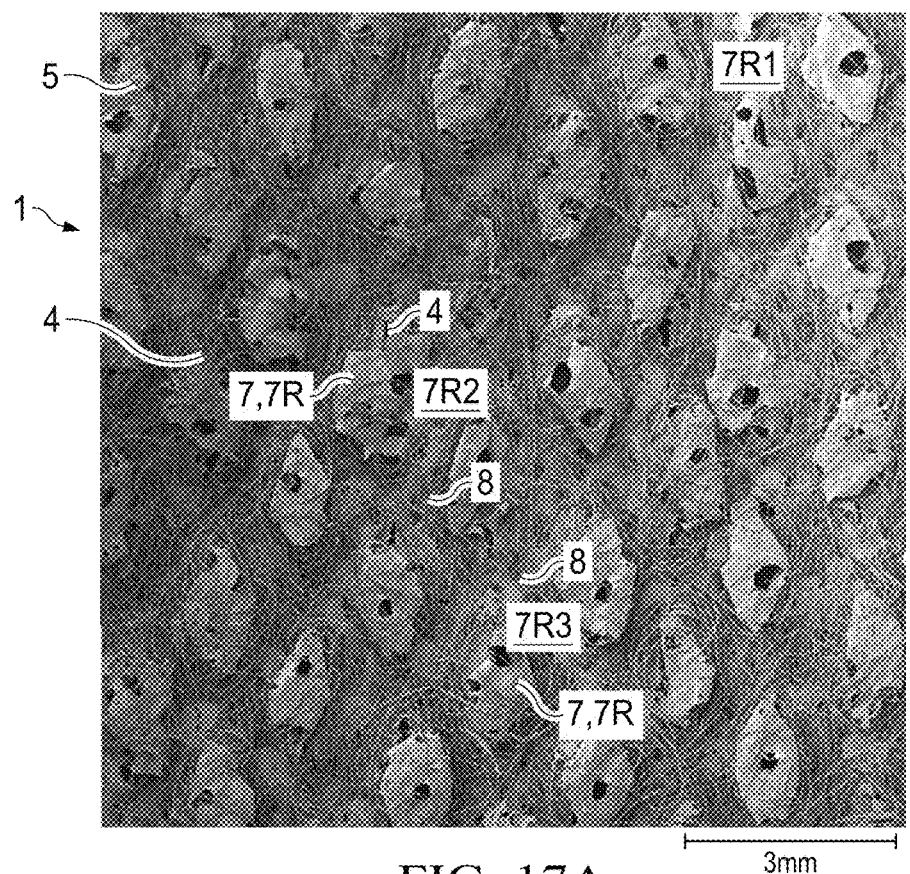
FIG. 17A is a plan view of a nonwoven side scanning electron microscope image of a laminate web having recesses according to the present invention.
Figure 17B:
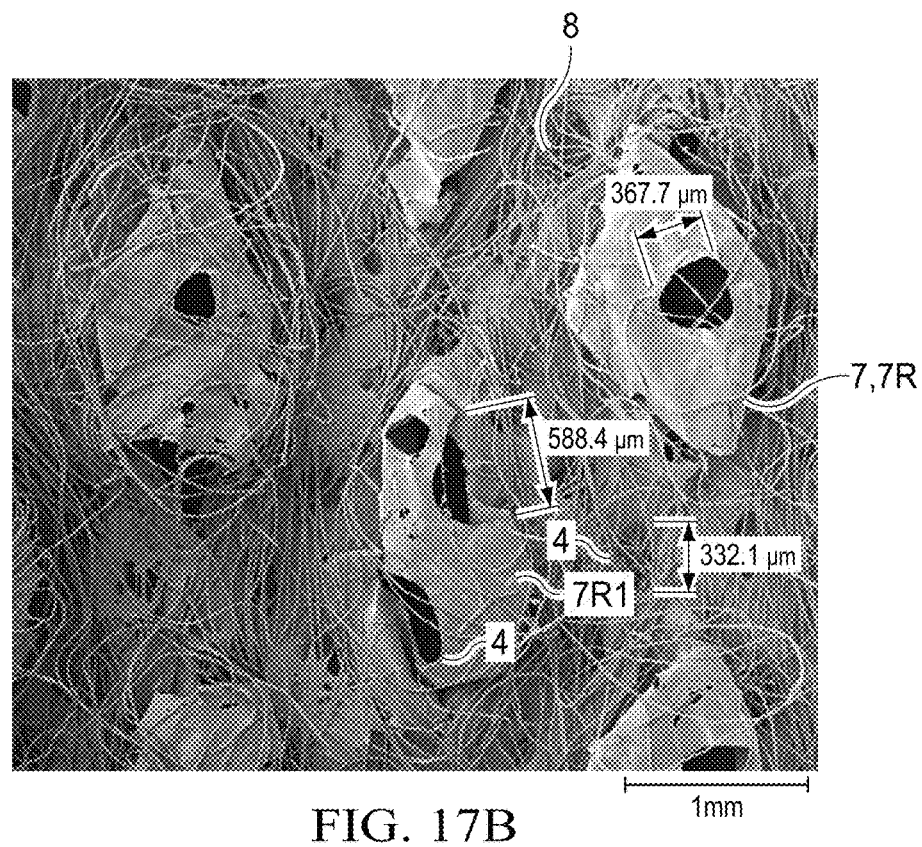
FIGS. 17B-17D are plan views of higher magnitude scanning electron microscope images of the laminate web of FIG. 17A.
Figure 17C:
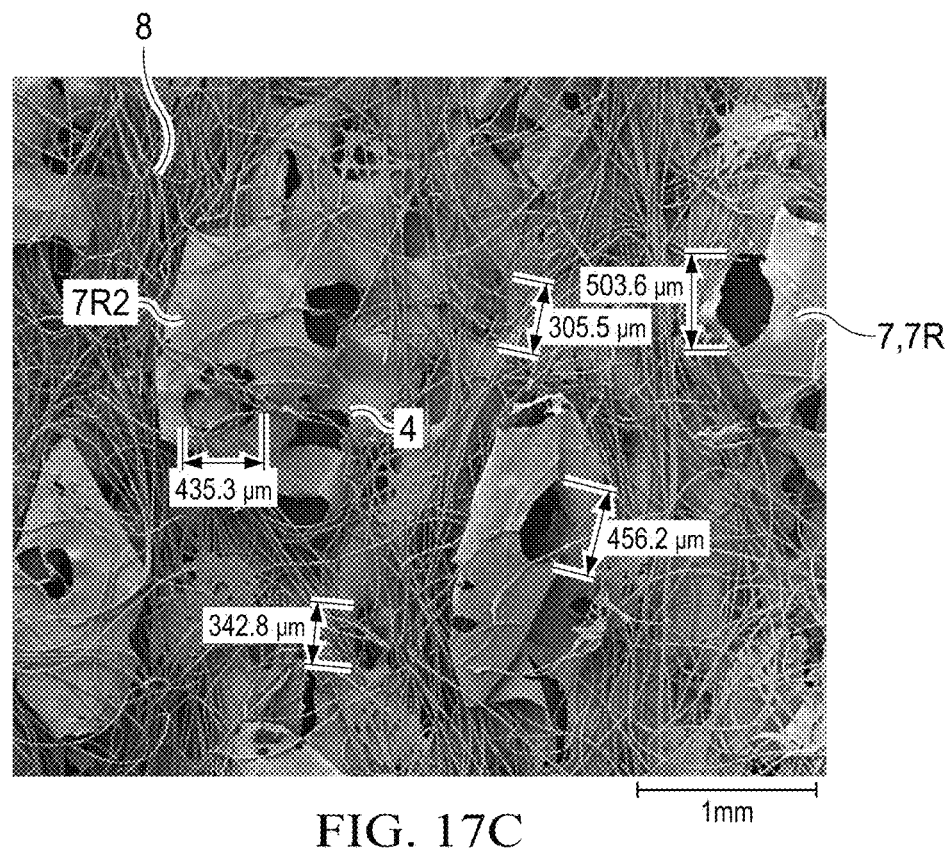
Figure 17D:
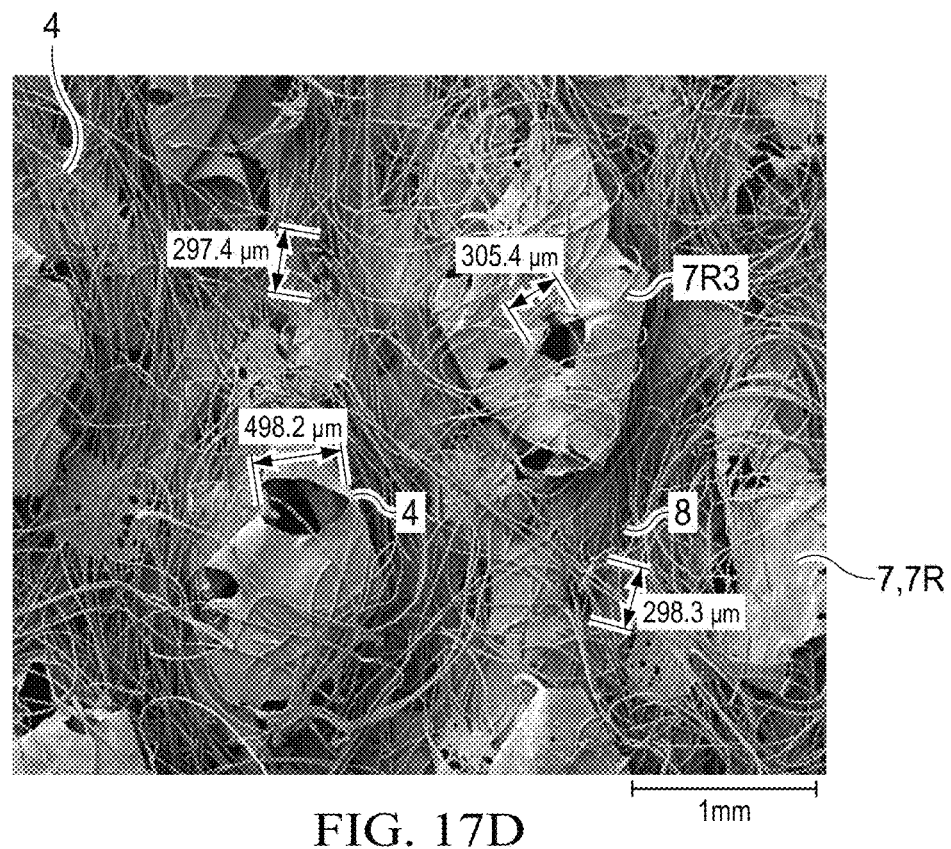

FIG. 17A is a SEM (Quanta 450, FEI) image of highly magnified portions of a nonwoven layer side of laminate 8. FIGS. 17B-17D are SEM (Quanta 450, FEI) images of more highly magnified portions of FIG. 17A, including recesses 7R1, 7R2 and 7R3 indicated in FIG. 17A, respectively.

Figure 18A:
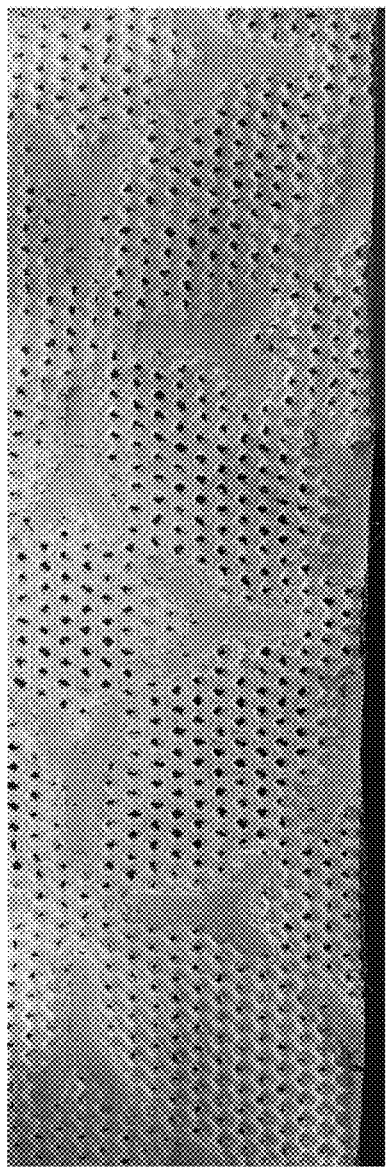
FIG. 18A is a plan view of a film side light microscope image of a laminate topsheet of a commercially available sanitary napkin.
Figure 18B:
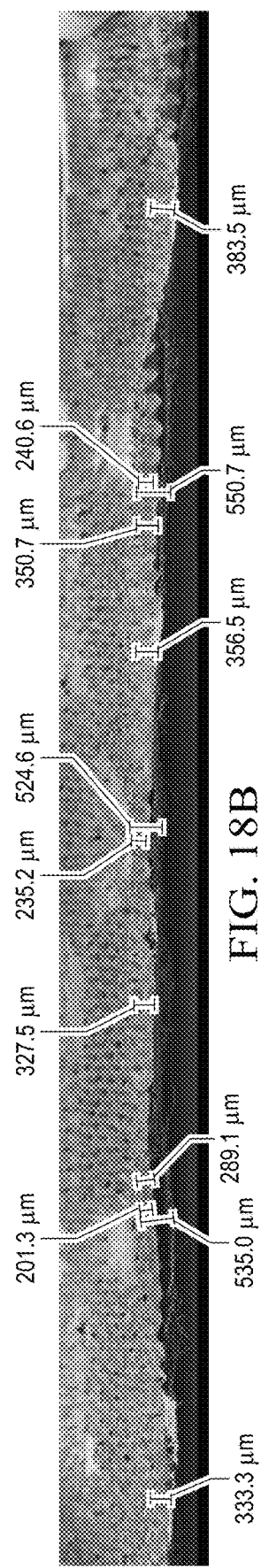
FIG. 18B is a plan view of a microscopic image of a cross section of the web of FIG. 18A.

Sanitary napkin samples 7 and 8 were prepared using Always Thin Long Super with Wing (Procter and Gamble Company, US) according to the preparation disclosed in Example 1 with topsheets formed by laminate 7 and laminate 8 produced above, respectively. Sample 9 was prepared using Always Thin Long Super with Wing (Procter and Gamble Company, US) by removing a topsheets and using a topsheet removed from a commercially available sanitary pad, Dollar General Health Ultra Thin Long Super with Wings (hereinafter "DG Ultra") (First Quality, US). FIGS. 18A and 18B are a light microscope (Discovery V20 Stereolight microscope with a MRCS Camera, Zeiss) images of a film side (skin-facing side) of the removed topsheet and a cross section thereof. It was observed that the Y-shape embossed areas were compressed and flat, and had substantially no apertures. Samples were allowed to equilibrate to the controlled room temperature for at least two hours prior to testing.

Example 3: Acquisition Time

Acquisition times of samples 1-7 and 9 obtained in Examples 1 and 2 were measured according to Acquisition Time Measurement described under TEST METHODS above and results are indicated in Table 1.

TABLE 1

|  | Sample 1 | Sample 2 | Sample 3 | Sample 4 | Sample 5 |
| --- | --- | --- | --- | --- | --- |
| Topsheet | Laminate 1 (film/6denier nonwoven) | Laminate 2 (film/3denier nonwoven) | Laminate 3 (film/2.5denier spunbond nonwoven) | Laminate 4 (film/6denier nonwoven) | Laminate 5 (film/3denier nonwoven) |
| Topsheet 3D structure | First elements and protrusions | First elements and protrusions | First elements and protrusions | First elements only | First elements only |
| Acquisition time (sec) | 9.63 | 8.37 | 11.03 | 25.3 | 16.1 |

|  | Sample 6 | Sample 7 | Sample 9 |
| --- | --- | --- | --- |
| Topsheet construction | Laminate 6 (film/2.5denier spunbondnonwoven) | Laminate 7 (film/6denier nonwoven) | Film/nonwoven |
| Topsheet 3D structure | First elements only | First elements and recesses | apertures and embossing |
| Acquisition time (sec) | 21.3 | 19.3 | 30.4 |

Acquisition times of sample 8 and sample 6 were separately measured according to Acquisition Time Measurement described under TEST METHODS above and results are indicated in Table 2.

TABLE 2

|  | Sample 8 | Sample 6 |
| --- | --- | --- |
| Topsheet construction | Laminate 8 (film/2.5denier spunbond nonwoven) | Laminate 6 (film/2.5denier spunbond nonwoven) |
| Topsheet 3D structure | First elements and recesses | First elements only |
| Acquisition time (sec) | 18.15 | 28.95 |

Example 4: Stain Perception

Mean Chromas of samples 1-7 and 9 obtained in Examples 1 and 2 were measured at 5 minute time point according to Stain Perception Measurement under TEST METHODS above, and are indicated in Table 3.

TABLE 3

|  | Sample 1 | Sample 2 | Sample 3 | Sample 4 | Sample 5 | Sample 6 | Sample 7 | Sample 9 |
| --- | --- | --- | --- | --- | --- | --- | --- | --- |
| Mean Chroma after 5 min | 12.17 | 13.10 | 12.83 | 14.85 | 44.49 | 40.27 | 9.13 | 22.80 |

Figure 31:
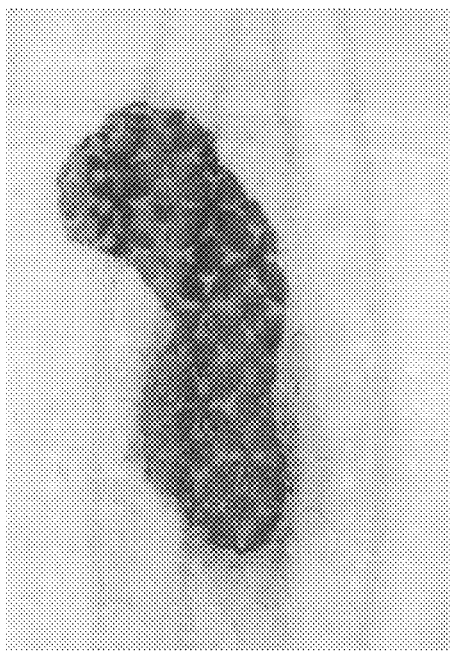
FIG. 31 is a plan view microscopic image of a commercially available sanitary napkin according to the Stain Perception Measurement.

FIGS. 22-28 are macroscopic images of samples 1-7 and FIG. 31 is a macroscopic image of sample 9 obtained at 5 minute time point obtained in the Stain Perception Measurement under TEST METHODS above.

Mean chromas of sample 8 obtained in Example 2 and sample 6 obtained in Example 1 were measured at 5 minute time point according to Stain Perception Measurement under TEST METHODS above, and are indicated in Table 4.

TABLE 4

|  | Sample 8 | Sample 6 |
| --- | --- | --- |
| Mean Chroma after 5 min | 16.89 | 44.96 |

Figure 29:
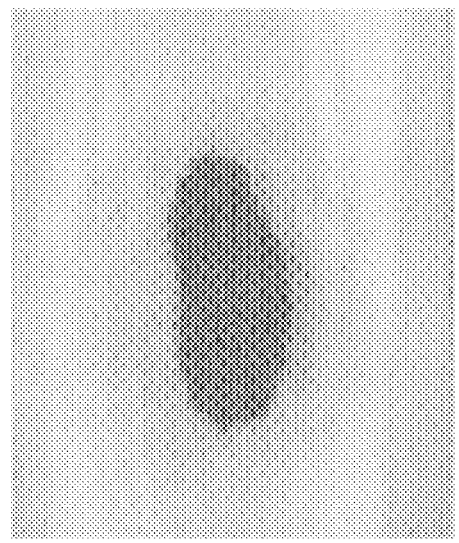
FIG. 29 is a plan view microscopic image of another sanitary napkin according to the Stain Perception Measurement.
Figure 30:
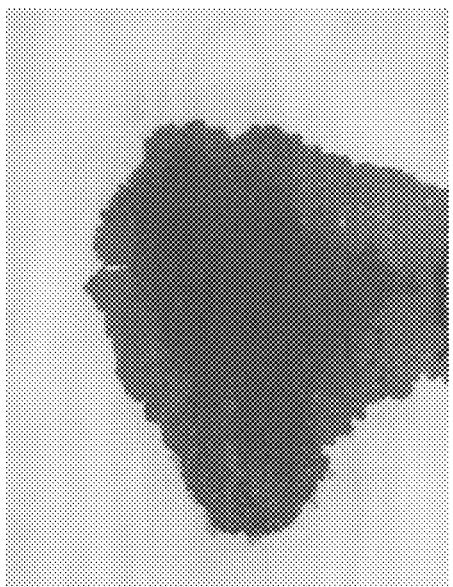
FIG. 30 is a plan view microscopic image of another sanitary napkin according to the Stain Perception Measurement.

FIGS. 29 and 30 are microscopic images of samples 8 and 6, respectively obtained at 5 minute time points obtained in the Stain Perception Measurement.

Example 5: Sample Preparation III

Laminate 10 having a plurality of first elements (70 mesh) and a plurality of apertures (28 to 29 apertures/cm$^2$) as second elements was produced according to a process schematically depicted in FIG. 6B against second element forming unit similar to one shown in FIG. 12. 15 gsm air-through carded nonwoven produced from 6 denier PE/PET bicomponent fibers, and 12 gsm polymer film produced from polyethylene resin using a film extruder were used to produce laminate 10. The carded nonwoven with a high caliper was produced by optimizing nonwoven production conditions such as oven air flow temperature, hot air pressure and web tension when going through the oven and/or calendar rolls. The carded nonwoven was supplied onto the second surface of the polymer film to form a precursor laminate while the film was still hot enough to bond to the nonwoven.

Laminate 11 having the same discrete extended elements (70 mesh) and apertures (28 to 29 apertures/cm$^2$) as those for laminate 10 was produced according to a process schematically depicted in FIG. 6B having equipment of FIG. 12 using 10 gsm spunbond nonwoven produced from 2.5 denier PP fibers, and 12 gsm polymer film produced from polyethylene resin using a film extruder.

Polymer film 1 having the same discrete extended elements (70 mesh) and apertures (24 to 25 apertures/cm$^2$) was produced using 22.4 gsm polymer film produced from polyethylene resin using a film extruder.

Figure 20:
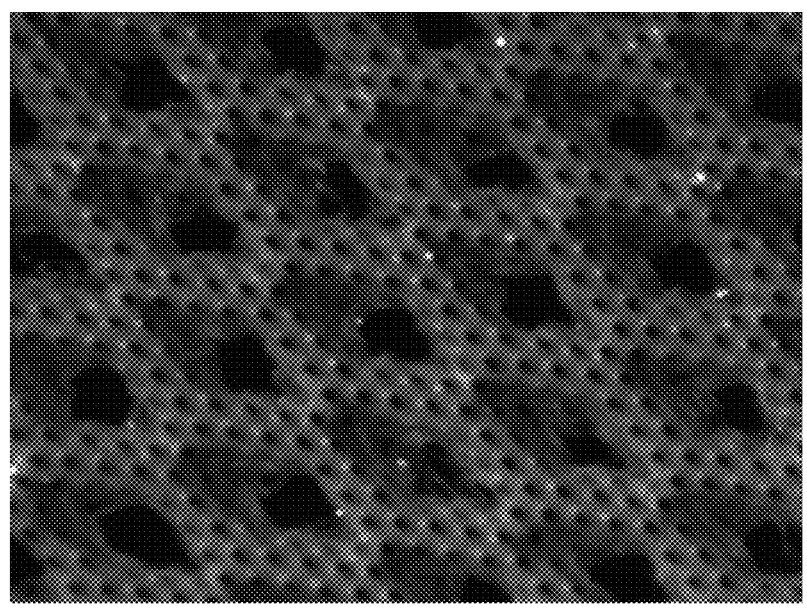
FIG. 20 is a microscopic image of a film layer of a laminate.
Figure 21A:
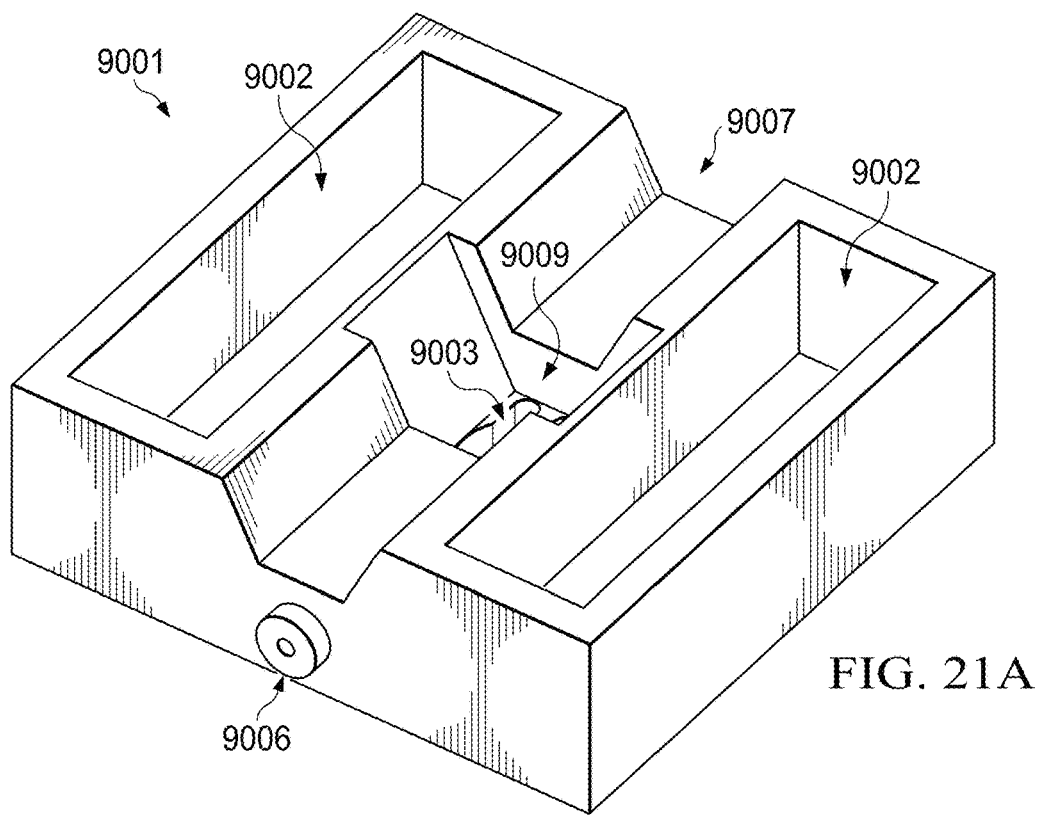
FIG. 21A is a perspective view of a strikethrough plate for acquisition time measurement.
Figure 21B:
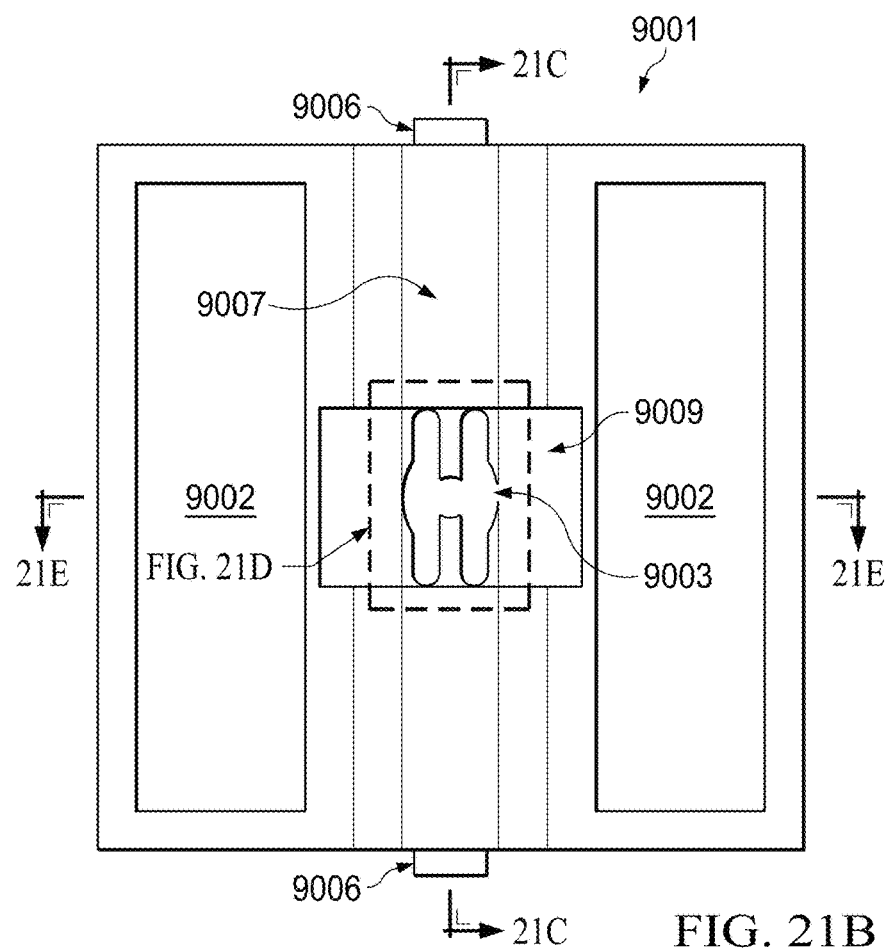
FIG. 21B is a plan view of the strikethrough plate of FIG. 21A.
Figure 21C:
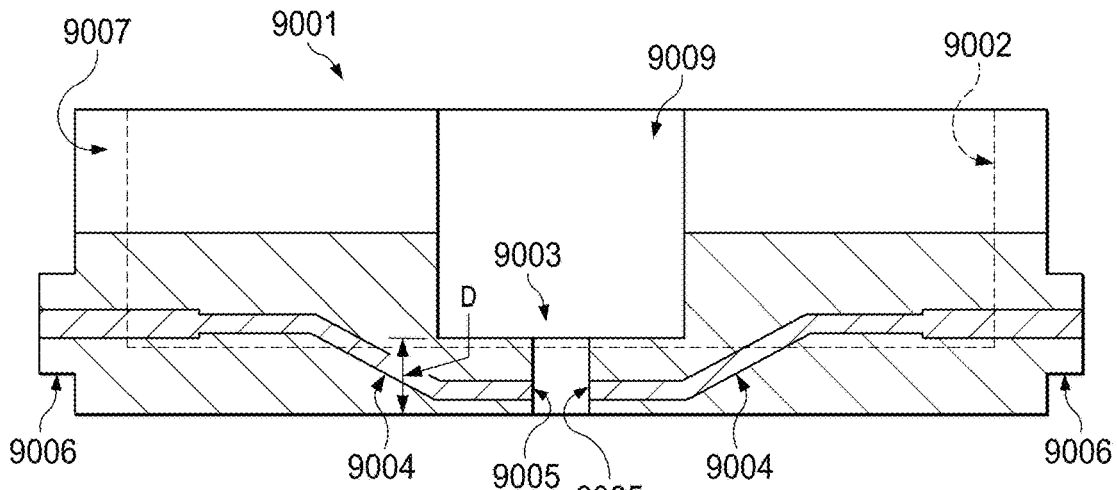
FIG. 21C is a plan view of a 21C-21C direction cross section of the strikethrough plate of FIG. 21B.
Figure 21D:
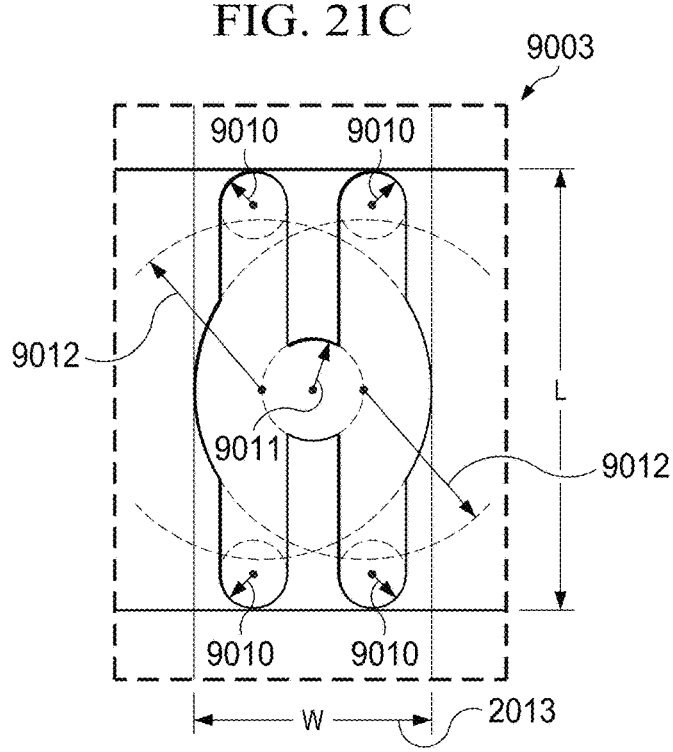
FIG. 21D is a plan view of part pf the strikethrough plate of FIG. 21B.
Figure 21E:
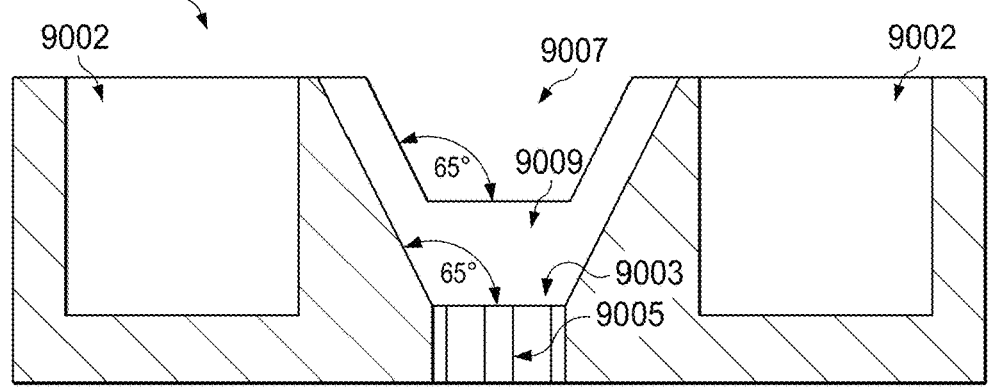
FIG. 21E is a plan view of a 21E-21E direction cross section of the strikethrough plate of FIG. 21B.
Figure 22:
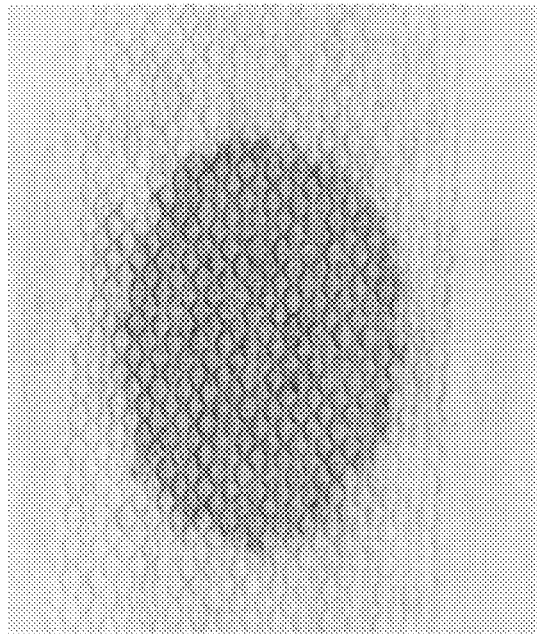
FIG. 22 is a plan view microscopic image of a sanitary napkin according to the Stain Perception Measurement.
Figure 23:
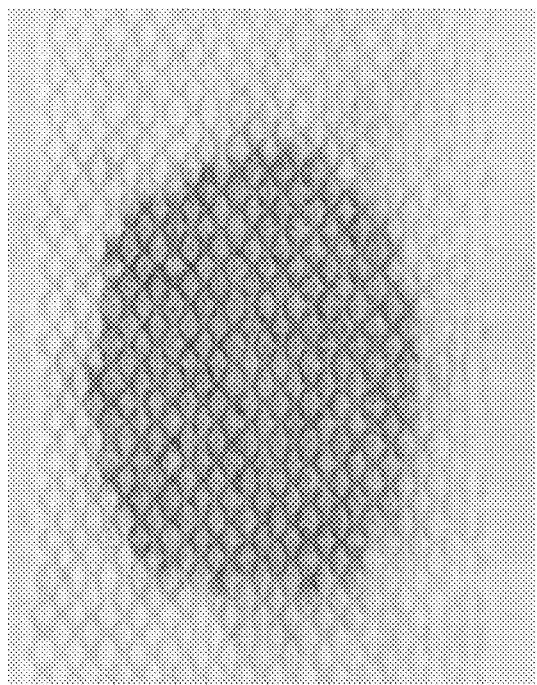
FIG. 23 is a plan view microscopic image of another sanitary napkin according to the Stain Perception Measurement.
Figure 24:
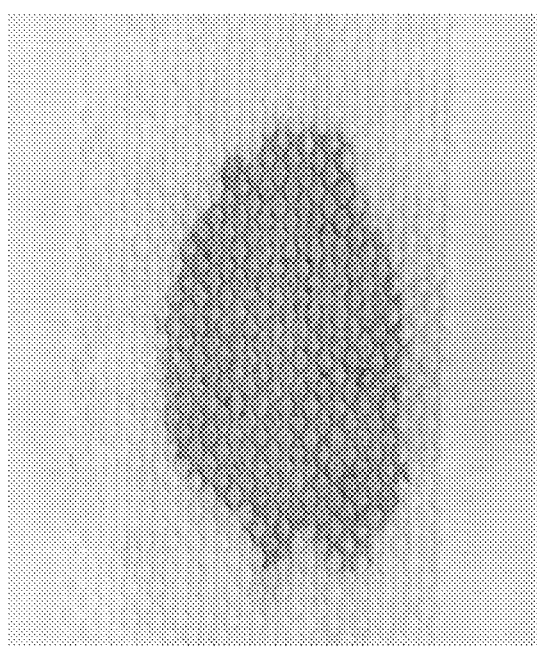
FIG. 24 is a plan view microscopic image of another sanitary napkin according to the Stain Perception Measurement.
Figure 25:
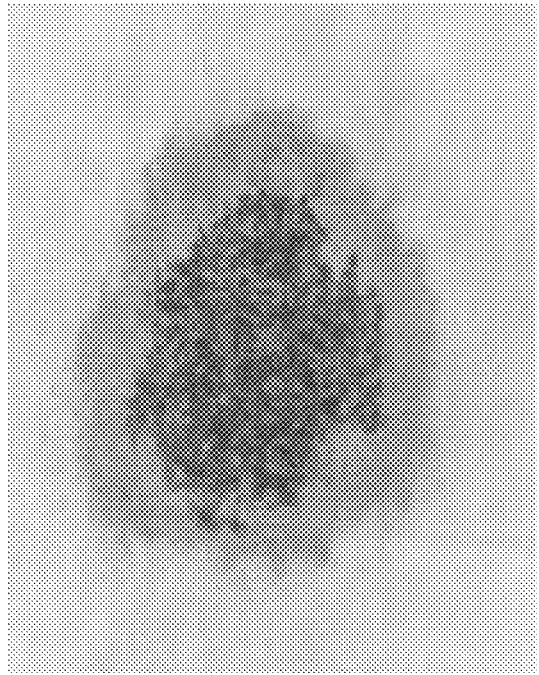
FIG. 25 is a plan view microscopic image of another sanitary napkin according to the Stain Perception Measurement.
Figure 26:
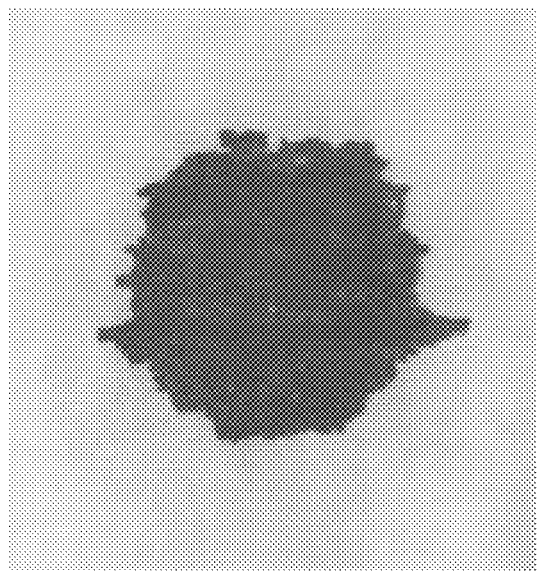
FIG. 26 is a plan view microscopic image of another sanitary napkin according to the Stain Perception Measurement.
Figure 27:
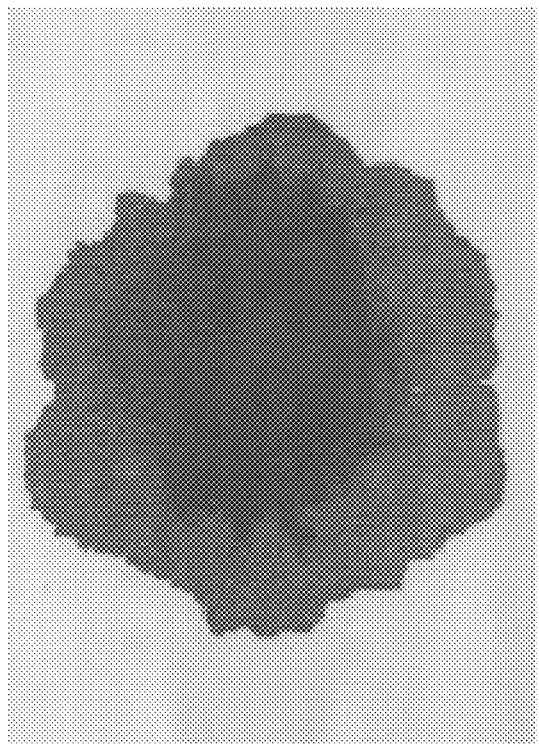
FIG. 27 is a plan view microscopic image of another sanitary napkin according to the Stain Perception Measurement.
Figure 28:
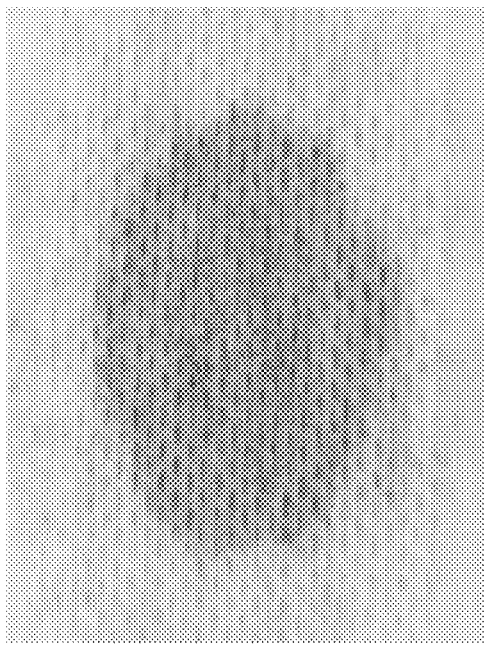
FIG. 28 is a plan view microscopic image of another sanitary napkin according to the Stain Perception Measurement.

FIGS. 19 and 20 are 20× light microscope (Discovery V20 Stereolight microscope with a MRCS Camera, Zeiss) images of film sides of laminate 10 and polymer film 1, respectively.

Sanitary napkin samples 10, 11 and 12 were produced according to the method described in Example 1 using topsheets formed by laminates 10 and 11, and polymer film 1, respectively. Samples were allowed to equilibrate to the controlled room temperature for at least two hours prior to testing.

Example 6: Acquisition time and stain perception

Acquisition times of samples 10 and 11 were measured according to Acquisition Time Measurement under TEST METHODS above, and results are indicated in Table 5. Mean chromas of samples 10 and 11 were measured according to Stain Perception Measurement at 2 minute time point under TEST METHODS above, and results are indicated in Table 5.

TABLE 5

|  | Sample 10 | Sample 11 |
| --- | --- | --- |
| Film layer | PE film, 12 gsm | PE film, 12 gsm |
| Nonwoven layer | Carded nonwoven formed by 6 denier PE/PET bico polymers, 15 gsm | Spunbond nonwoven formed by 2.5 denier PP polymer, 10 gsm |
| First element | discrete extended elements | discrete extended elements |
| Second element | Apertures | Apertures |
| Acquisition time (sec) | 12.4 | 16.5 |
| Mean Chrom after 2 min | 13.4 | 17.8 |

Figure 32:
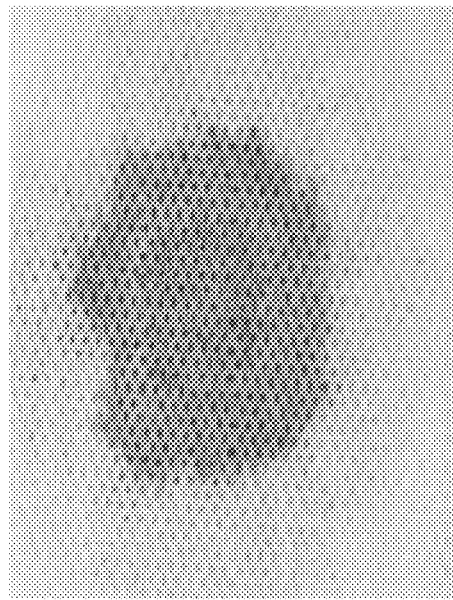
FIG. 32 is a plan view microscopic image of another sanitary napkin according to the Stain Perception Measurement.
Figure 33:
FIG. 33 is a plan view microscopic image of another sanitary napkin according to the Stain Perception Measurement.

FIGS. 32 and 33 are microscopic images of sample 10 and comparative sample 11, respectively, obtained at 2 minute time point obtained in the Stain Perception Measurement under TEST METHODS above.

Example 7: Fiber-Fiber Distance

Fiber to fiber distances in z-direction in nonwoven layers of samples 10 and 11 were measured according to Fiber-Fiber Distance Measurement described under TEST METHODS above and results are indicated in Table 6.

TABLE 6

|  | Sample 10 | Sample 11 |
| --- | --- | --- |
| Fiber-Fiber distance in nonwoven layer (μm) | 108 | 48 |

Example 8: Softness

Softness of samples 10 and 12 was measured using product characteristics including those specified in Table 7 with 17 sensory panels extensively trained to rate the intensity of the discrete product characteristics on a 0-100 using all their senses. Data is reported as means for the entire group. Results are shown in Table 7 below. Sample 10 with a 12 gsm film layer skin-facing surface shows favorable scores in all four items compared to sample 12, a 22.4 gsm film layer in a skin-facing surface.

TABLE 7

|  | Sample 2 | Comparative Sample 3 |
| --- | --- | --- |
| Fuzzy Feel | 10.2 | 1.7 |
| Plastic Feel | 35.5 | 58.6 |
| Cottony Feel | 31.1 | 15.7 |
| Rough Feel | 22.0 | 46.1 |

All attributes were assessed on a 0-100 pt scale for intensity anchored as 0=none, 50=moderate, 100=extremely high.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a liquid permeable topsheet, a liquid impermeable backsheet, and an absorbent core disposed between the topsheet and the backsheet, wherein the topsheet comprises a laminate web comprising a first layer comprising an extruded polymer film and a second layer comprising a nonwoven web, wherein the polymer film and the nonwoven web have been joined to form a precursor laminate while the film was in a softened state thereby to bond to the nonwoven, the precursor laminate having a first side defined by the polymer film, and an opposing second side defined by the nonwoven;

wherein the first layer has a pattern of relatively smaller apertures formed therethrough, wherein the apertures have a diameter of less than about 500 microns, and wherein the first layer comprises at least about 95 discrete apertures per square centimeter, wherein the laminate has a pattern of relatively larger protrusions formed therein, wherein each of the first layer and the second layer form the larger protrusions, wherein the relatively larger protrusions being of a size sufficient for a plurality of the relatively smaller apertures to be present within each of a plurality of the protrusions, wherein each large protrusion defines a void area interiorly, wherein each of the larger protrusions has a base, wherein the base and the first side are coplanar, wherein each of the larger protrusions comprises a plateau and a sidewall extending from the plateau to the base, wherein the base is wider than the plateau, and wherein the first layer is stretched to form the larger protrusions such that a portion of the first layer forming the larger protrusion has a reduced thickness as compared to the base and such that the apertures present within each of the plurality of protrusions are enlarged relative to the apertures present elsewhere on the first layer;

wherein the first layer is an outer most layer of the absorbent article facing the skin of a wearer;

wherein the pattern of relatively smaller apertures and the pattern of relatively larger protrusions extends throughout the liquid permeable topsheet;

wherein the nonwoven web comprises a carded nonwoven comprising bicomponent fibers.

2. The absorbent article of claim 1, wherein the apertures have an area of between about 0.01 mm$^2$ and about 0.78 mm$^2$.

3. The absorbent article of claim 1, wherein the density of the protrusions is from about 20 to about 40 second elements/cm$^2$ laminate web.

4. The absorbent article of claim 1, wherein the first layer has a basis weight of about 18 gsm or less.

5. The absorbent article of claim 1, wherein the nonwoven layer has a basis weight of about 30 gsm or less.

6. The absorbent article of claim 1, wherein the nonwoven web is either thermally bonded or air through bonded.

7. The absorbent article of claim 1, wherein the nonwoven web is a carded air through bonded nonwoven formed of polymer fibers having a fiber thickness of no less than 5 denier.

8. The absorbent article of claim 1, wherein the nonwoven web is a carded air through bonded nonwoven web comprising 6 denier fibers.

* * * * *